United States Patent [19]

Kaplan et al.

[11] Patent Number: 5,306,289

[45] Date of Patent: * Apr. 26, 1994

[54] BRAIDED SUTURE OF IMPROVED CHARACTERISTICS

[75] Inventors: Donald S. Kaplan, Weston; Matthew E. Hermes, Easton; Ross R. Muth, Brookfield, all of Conn.

[73] Assignee: United States Surgical Corporation, Norwalk, Conn.

[ * ] Notice: The portion of the term of this patent subsequent to May 28, 2008 has been disclaimed.

[21] Appl. No.: 658,681

[22] Filed: Feb. 26, 1991

Related U.S. Application Data

[63] Continuation-in-part of Ser. No. 569,062, Aug. 17, 1990, abandoned, and Ser. No. 529,740, May 22, 1990, Pat. No. 5,037,429, and Ser. No. 491,215, Mar. 9, 1990, Pat. No. 5,019,093, which is a continuation of Ser. No. 344,745, Apr. 18, 1989, abandoned, which is a continuation-in-part of Ser. No. 227,699, Aug. 3, 1988, abandoned, which is a continuation-in-part of Ser. No. 89,732, Aug. 26, 1987, abandoned, said Ser. No. 529,740, is a continuation of Ser. No. 89,735, Aug. 26, 1987, abandoned, and a continuation-in-part of Ser. No. 221,308, Jul. 13, 1988, Pat. No. 5,051,272, and Ser. No. 395,476, Aug. 18, 1989, abandoned, and Ser. No. 89,733, Aug. 26, 1987, abandoned, and Ser. No. 393,017, Aug. 10, 1989, abandoned, which is a continuation of Ser. No. 89,734, Aug. 26, 1987, abandoned.

[51] Int. Cl.⁵ ............................................. A61B 17/00
[52] U.S. Cl. ................................. 606/228; 606/230; 606/231
[58] Field of Search ...................... 606/228–231; 428/378, 392, 394; 424/422, 423, 424, 444; 523/114; 530/399

[56] References Cited

U.S. PATENT DOCUMENTS

| Re. 28,281 | 11/1965 | Bridgeford . |
|---|---|---|
| 2,917,410 | 12/1959 | Vitalls . |
| 3,009,893 | 11/1961 | Barnes et al. . |
| 3,125,095 | 3/1964 | Kaufman et al. . |
| 3,187,752 | 6/1965 | Glick . |
| 3,297,033 | 1/1967 | Schmitt et al. . |
| 3,359,983 | 12/1967 | Northey . |
| 3,371,069 | 2/1968 | Miyamae et al. . |
| 3,413,079 | 11/1968 | Rich, Jr. . |
| 3,565,077 | 2/1971 | Glick . |
| 3,626,948 | 12/1971 | Glick et al. . |

(List continued on next page.)

FOREIGN PATENT DOCUMENTS

| 0046039 | 2/1982 | European Pat. Off. . |
|---|---|---|
| 0128733 | 12/1984 | European Pat. Off. . |
| 0131868 | 1/1985 | European Pat. Off. . |
| 0177915 | 4/1986 | European Pat. Off. . |
| 0267015 | 5/1988 | European Pat. Off. . |
| WO83/04030 | 11/1983 | PCT Int'l Appl. . |
| WO85/00369 | 1/1985 | PCT Int'l Appl. . |
| WO86/02271 | 4/1986 | PCT Int'l Appl. . |
| 2092444A | 2/1982 | United Kingdom . |
| 2082213A | 3/1982 | United Kingdom . |
| 2092155 | 8/1982 | United Kingdom . |
| 2162851 | 7/1984 | United Kingdom . |

OTHER PUBLICATIONS

Brown et al., "Acceleration of Tensile Strength of Incisions Treated with EGF and TGF-beta", Ann. Surg., pp. 788 et seq. (Dec. 1988).

Barbul et al., eds., "Growth Factors and Other Aspects of Wound Healing/Biological and Clinical Implications", *Proceedings of the Second International Symposium on Tissue Repair*, Tarpon Springs, Florida, May 13–17, 1987 (Alan R. Liss, Inc., New York).

Biochemistry 1981, 20, 4667–4686.

Lynch et al., "Growth Factors in Wound Healing" *J. Clin. Invest.*, vol. 84, Aug. 1989, 640–646.

Primary Examiner—Stephen C. Pellegrino
Assistant Examiner—Gary Jackson
Attorney, Agent, or Firm—Thomas R. Bremer; Peter G. Dilworth; Rocco S. Barrese

[57] ABSTRACT

A braided suture exhibits one or more improved properties, e.g., reduced chatter, greater flexibility and/or better hand, than that of a braided suture of known, or standard, construction and of substantially equivalent size.

61 Claims, 12 Drawing Sheets

U.S. PATENT DOCUMENTS

| | | |
|---|---|---|
| 3,636,956 | 1/1972 | Schneider . |
| 3,655,927 | 4/1972 | Samuelson et al. . |
| 3,728,839 | 4/1973 | Glick . |
| 3,772,420 | 11/1973 | Glick et al. . |
| 3,839,500 | 10/1974 | Dexter . |
| 3,839,524 | 10/1974 | Adams et al. . |
| 3,849,185 | 11/1974 | Shepherd et al. . |
| 3,883,497 | 5/1975 | Gregory et al. . |
| 3,896,814 | 7/1975 | Vivien et al. . |
| 3,917,740 | 11/1975 | Siclari et al. . |
| 3,917,824 | 11/1975 | Camble et al. . |
| 3,942,532 | 3/1976 | Hunter et al. . |
| 3,948,875 | 4/1976 | Cohen et al. . |
| 3,949,755 | 4/1976 | Vauquois . |
| 3,949,756 | 4/1976 | Ace . |
| 3,991,766 | 11/1976 | Schmitt et al. . |
| 4,013,773 | 3/1977 | Murakami et al. . |
| 4,014,433 | 3/1977 | Cerwin . |
| 4,014,973 | 3/1977 | Thompson . |
| 4,024,871 | 5/1977 | Stephenson . |
| 4,027,676 | 6/1977 | Mattei . |
| 4,043,344 | 8/1977 | Landi et al. . |
| 4,047,533 | 9/1977 | Perciaccante et al. . |
| 4,052,988 | 10/1977 | Doddi et al. . |
| 4,080,969 | 3/1978 | Casey et al. . |
| 4,081,493 | 3/1978 | Kazama et al. . |
| 4,105,034 | 9/1978 | Shalaby et al. . |
| 4,126,428 | 11/1978 | Rude . |
| 4,135,622 | 1/1979 | Glick . |
| 4,141,087 | 2/1979 | Shalaby et al. . |
| 4,157,085 | 6/1979 | Austad . |
| 4,162,242 | 7/1979 | House . |
| 4,179,337 | 12/1979 | Davis et al. . |
| 4,185,637 | 1/1980 | Mattei . |
| 4,201,216 | 5/1980 | Mattei . |
| 4,204,542 | 5/1980 | Bokros et al. . |
| 4,206,101 | 6/1980 | Wysong . |
| 4,321,038 | 3/1982 | Porteous . |
| 4,330,338 | 5/1982 | Banker . |
| 4,362,162 | 12/1982 | Nakajima et al. . |
| 4,363,319 | 12/1982 | Altshuler . |
| 4,412,986 | 11/1983 | Kawata et al. . |
| 4,432,964 | 2/1984 | Shell et al. . |
| 4,439,181 | 3/1984 | Blackshear et al. . |
| 4,444,927 | 4/1984 | Borysko . |
| 4,452,973 | 6/1984 | Casey et al. . |
| 4,466,431 | 8/1984 | Tharrat et al. . |
| 4,469,837 | 9/1984 | Cattaneo . |
| 4,523,591 | 6/1985 | Kaplan et al. . |
| 4,528,186 | 7/1985 | Nishimura et al. . |
| 4,532,929 | 8/1985 | Mattei et al. . |
| 4,546,769 | 10/1985 | Planck et al. . |
| 4,579,731 | 4/1986 | Fox, Jr. et al. . |
| 4,588,400 | 5/1986 | Ring et al. . |
| 4,594,240 | 6/1986 | Kawata et al. . |
| 4,600,743 | 7/1986 | Shizuki et al. . |
| 4,620,974 | 11/1986 | Hersch et al. . |
| 4,621,052 | 11/1986 | Sugimoto . |
| 4,621,638 | 11/1986 | Silvestrini . |
| 4,624,256 | 11/1986 | Messier et al. . |
| 4,649,920 | 3/1987 | Rhum . |
| 4,653,497 | 3/1987 | Bezwada et al. . |
| 4,705,820 | 11/1987 | Wang et al. . |
| 4,711,241 | 12/1987 | Lehmann . |
| 4,717,717 | 1/1988 | Finkenaur . |
| 4,742,003 | 5/1988 | Derynck et al. . |
| 4,743,679 | 5/1988 | Cohen et al. . |
| 4,792,336 | 12/1988 | Hlavacek et al. . |
| 4,801,456 | 1/1989 | Drengler . |
| 4,806,621 | 2/1989 | Kohn et al. . |
| 4,857,602 | 8/1989 | Casey et al. . |
| 4,861,757 | 8/1989 | Antoniades et al. . |
| 4,874,746 | 10/1989 | Antoniades et al. . |
| 4,906,474 | 3/1990 | Langer et al. . |
| 4,911,908 | 3/1990 | Estis et al. . |
| 4,913,903 | 4/1990 | Sudmann et al. . |
| 4,917,685 | 4/1990 | Viswanathan et al. . |
| 4,929,242 | 5/1990 | Powell . |
| 4,944,948 | 7/1990 | Uster et al. . |
| 5,019,093 | 5/1991 | Kaplan et al. ............... 606/228 |
| 5,037,429 | 8/1991 | Hermes et al. ............... 606/230 |
| 5,051,272 | 9/1991 | Hermes et al. ............... 427/2 |
| 5,059,213 | 10/1991 | Chesterfield et al. ............... 606/228 |
| 5,181,923 | 1/1993 | Chesterfield et al. ............... 606/228 |

STEP 1

STEP 2

STEP 3

BRAIDED SUTURE OF IMPROVED CHARACTERISTICS

This application is a continuation-in-part of copending U.S. patent application Ser. No. 569,062, filed Aug. 17, 1990 now abandoned, and copending U.S. patent application Ser. No. 491,215, filed Mar. 9, 1990, now U.S. Pat. No. 5,019,093 as a continuation of then copending and now abandoned U.S. patent application Ser. No. 344,745, filed Apr. 18, 1988, now abandoned as a continuation-in-part of then copending and now abandoned U.S. patent application Ser. No. 227,699, filed Aug. 3, 1988, now abandoned as a continuation-in-part of then copending and now abandoned U.S. patent application Ser. No. 89,732, filed Aug. 26, 1987, now abandoned. This application is also a continuation-in-part of copending U.S. patent application Ser. No. 529,740, filed May 22, 1900 now U.S. Pat. No. 5,037,429 as a continuation of then copending and now abandoned U.S. patent application Ser. No. 89,735, filed Aug. 26, 1987, a continuation-in-part of U.S. patent application Ser. Nos. 221,308, filed Jul. 13, 1988, now U.S. Pat. No. 5,052,727 and 395,476, filed Aug. 18, 1989, now abandoned and a continuation-in-part of copending U.S. patent application Ser. Nos. 89,733 filed Aug. 26, 1987, abandoned and 393,017, filed Aug. 10, 1989, now abandoned, the latter filed as a continuation of then copending and now abandoned U.S. patent application Ser. No. 89,734, filed Aug. 26, 1987, now abandoned. This application also relates by subject matter to U.S. patent application Ser. Nos. 569,063, filed Aug. 17, 1990, 470,344, filed Aug. 21, 1990, U.S. Pat. No. 5,076,312, and 570,345, filed Aug. 21, 1990, now U.S. Pat. No. 5,133,738.

BACKGROUND OF THE INVENTION

This invention relates to a braided suture exhibiting one or more improved characteristics, e.g., reduced tissue drag, reduced chatter, greater flexibility and/or better hand than a known, or "standard", suture of substantially equivalent size.

Sutures intended for the repair of body tissues must meet certain requirements: they must be substantially non-toxic, capable of being readily sterilized, they must have good tensile strength and have acceptable knot-tying and knot-holding (knot security) characteristics and if the sutures are of the absorbable or biodegradable variety, the absorption or biodegradation of the suture must be closely controlled.

Sutures have been constructed from a wide variety of materials including surgical gut, silk, cotton, a polyolefin such as polypropylene, polyamide, polyglycolic acid, polyesters such as polyethylene terephthalate and glycolide-lactide copolymer, etc. Although the optimum structure of a suture is that of a monofilament, since certain materials of construction will only result in a stiff monofilament lacking acceptable knot-tying and knot-holding properties, sutures manufactured from such materials are preferably provided as braided structures. Thus, for example, sutures manufactured from silk, polyamide, polyester and bioabsorbable glycolide-lactide copolymer are usually provided as multifilament braids. Commercial examples of such sutures include those marketed under the DEXON (Davis & Geck, Inc.,) and VICRYL (Ethicon, Inc.) brands.

Currently available braided suture products are acceptable in terms of their knot-tying and knot-holding properties. However, as removed from the package, they tend to be stiff and wiry and retain a "set" or "memory" such that at the time of use, it is usually necessary for the surgeon or assistant personnel to flex and stretch the suture to make it more readily handible. Furthermore, the surfaces of known sutures are perceptibly rough. Thus, if one passes one's hand or fingers along the braid, surface irregularities will be readily detected. The result of this rough surface is that the suture will exhibit tissue drag and/or chatter as it is drawn through tissue, characteristics which militate against smooth, neat, accurately placed wound approximation, the hallmarks of excellence in surgical practice.

In the case of one braided suture now on the market, due to the necessity of having to meet fiber strength requirements while at the same time retaining acceptable knot-tying and knot-holding properties, the suture is constructed from a greater amount of fiber and consequently is of larger diameter than the accepted industry standard.

It is an object of this invention to provide a braided suture possessing one or more improved characteristics, e.g., reduced tissue drag, reduced chatter, greater flexibility and/or better hand than that of a known, or "standard", suture of substantially equivalent size.

It is another object of this invention to provide a braided suture which exhibits significantly better knot security, e.g., expressed in terms of knot pull strength and/or loop pull strength, compared with the knot security of a standard suture of substantially equivalent size.

It is a particular object of the invention to provide a braided suture exhibiting one or more of the foregoing improved characteristics possessing a greater number of sheath yarns, a finer denier for the individual filaments making up an individual sheath yarn and a greater pick count for a suture of any given overall denier.

SUMMARY OF THE INVENTION

By way of satisfying the foregoing objects as well as other objects of the invention, there is provided in accordance with this invention a braided suture exhibiting at least one improved property relative to a standard suture of substantially equivalent size, the improved property being that of reduced tissue drag, reduced chatter, greater flexibility, greater knot security and/or better hand.

As a result of its possessing a greater pick count and/or a greater number of sheath yarns for a suture of given overall denier and in some cases, a finer denier for the individual filaments making up a sheath yarn, the braided suture of the present invention exhibits fewer surface discontinuities thereby providing a suture which is considerably smoother than a standard braided suture. This smoother structure is believed to be responsible for the aforementioned improved characteristic(s).

The term "suture" is intended to embrace both the non-absorbable as well as the bioabsorbable varieties.

The term "braid" or "braided" as applied to the suture of this invention refers to an arrangement of discrete units, or bundles, denominated "sheath yarns", made up of individual filaments with individual sheath yarns interlocking or interlacing each other in a regular pattern, e.g., of criss-cross configuration.

The expression "pick count" refers to the number of crossovers or interlocks of sheath yarns per linear inch of suture and, together with the overall denier of the suture, the denier of the individual filaments constituting a sheath yarn and the number of sheath yarns employed, defines the principal construction characteristics of the braided suture herein.

The expression "standard suture" is intended to designate any of the heretofore known braided sutures, e.g., those described in U.S. Pat. No. 3,565,077, the contents of which are incorporated by reference herein, and in particular, braided suture products marketed by Ethicon, Inc. under its Vicryl brand and those marketed by Davis & Geck, Inc. (American Cyanamid Company) under its Dexon brand.

BRIEF DESCRIPTION OF THE DRAWINGS

The present invention will become more apparent from the following detailed description taken in conjunction with the accompanying illustrations in which.

DESCRIPTION OF THE PREFERRED EMBODIMENTS

Figure 1:
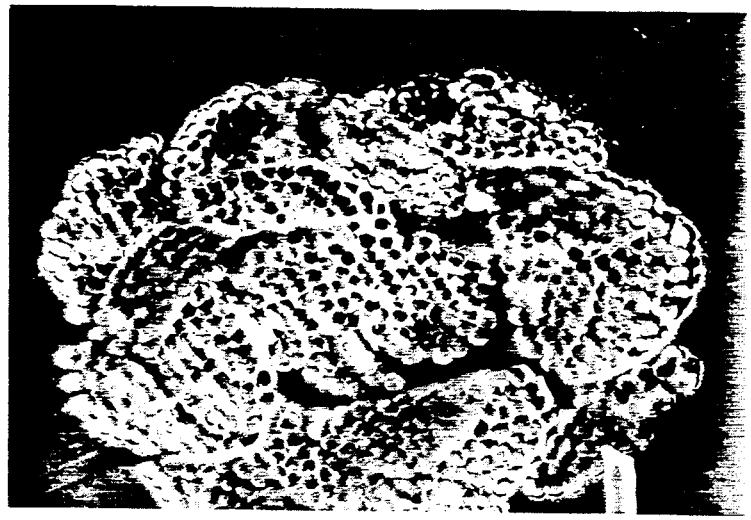
FIGS. 1, 2, 5 and 6 are photomicrographs of cross-sectional and linear views (FIGS. 2 and 6) of standard sutures which are presented for comparison purposes.
Figure 2:
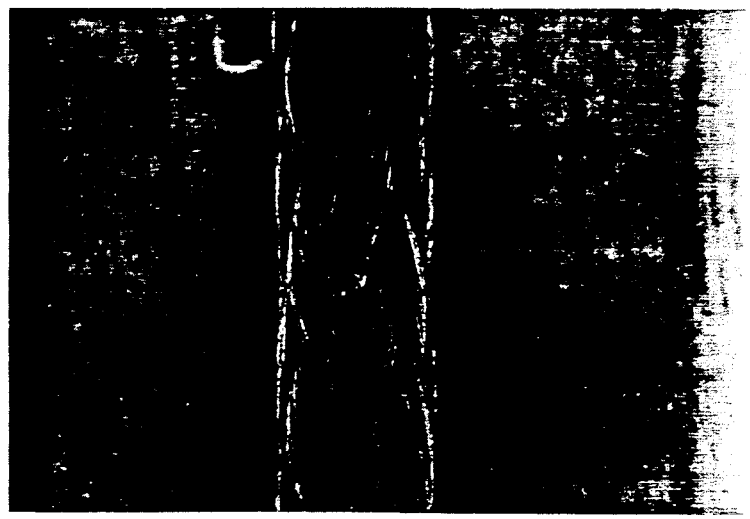
Figure 3:
FIGS. 3, 4 and 7 to 10 are photomicrographs of cross-sectional (FIGS. 3, 7 and 9) and linear views (FIGS. 4, 8 and 10) of braided sutures in accordance with the present invention.

In a preferred embodiment, the braided suture of the present invention is fabricated from a bioabsorbable or biodegradable resin such as one derived from polyglycolic acid, glycolide, lactic acid, lactide, dioxanone, trimethylene carbonate, etc., and various combinations of these and related monomers. Sutures prepared from resins of this type are known in the art, e.g., as disclosed in U.S. Pat. Nos. 2,668,162; 2,703,316; 2,758,987; 3,225,766; 3,297,033; 3,422,181; 3,531,561; 3,565,077; 3,565,869; 3,620,218; 3,626,948; 3,636,956; 3,736,646; 3,772,420; 3,773,919; 3,792,010; 3,797,499; 3,839,297; 3,867,190; 3,878,284; 3,982,543; 4,047,533; 4,060,089; 4,137,921; 4,157,437; 4,234,775; 4,237,920; 4,300,565; and, 4,523,591; U.K. Patent No. 779,291; D. K. Gilding et al., "Biodegradable polymers for use in surgery—polyglycolic/poly(lactic acid) homo- and co-polymers: 1, *Polymer*, Volume 20, pages 1459-1464 (1979), and D. F. Williams (ed.), *Biocompatibility of Clinical Implant Materials*, Vol. II, ch. 9: "Biodegradable Polymers" (1981).

The defining characteristics of a braided suture, apart from the material of its construction, are:

(1) overall suture denier;
(2) the pattern of the interlocking yarns expressed as the pick count, which is to say, the number of interlocks or crossovers of individual sheath yarns per linear inch of suture;
(3) the number of sheath yarns comprising the braid;
(4) the denier of the individual filaments comprising each sheath yarn; and,
(5) the denier of the core, where present.

In a preferred braided suture according to this invention, the foregoing construction characteristics are as follows:

(1) Overall Denier of the Suture

The overall denier of the suture can vary from about 50 to about 4000. Within this range, the ranges of overall denier for particular sutures are: from about 50 to about 125 denier; from above about 125 to about 200 denier; from above about 200 to about 300 denier; from above about 300 to about 500 denier; from above about 500 to about 800 denier; from above about 800 to about 1500 denier; from above about 1500 to about 2000 denier; and, from above about 2000 to about 3600 denier.

(2) Pattern of the Interlocking Sheath Yarns (Pick Count)

For a suture of any range of overall denier, pick count can vary from about 50 to about 100 crossovers/inch with about 55-80 crossovers/inch being preferred. For sutures constructed within any range of overall denier, as larger numbers of sheath yarns are employed, the pick-count for the sutures will also increase within the above ranges.

For a suture of a particular range of denier and number of sheath yarns, pick count is advantageously established to achieve a balance in the properties desired. In general, with increasing pick count, surface roughness of the suture tends to increase and with decreasing pick count, the ability of the external braided sheath to contain the core (if present) tends to decrease even reaching the point where the braid may become so loose as to result in the core protruding therethrough.

For sutures of any specific denier range and number of sheath yarns, it is preferable to have as low a pick count as possible in order to achieve optimum surface smoothness, consistent, of course, with the need to provide a compact braid which prevents the core (if present) from protruding through the exterior sheath yarn structure.

(3) The Number of Sheath Yarns

The number of sheath yarns bears some relation to overall suture denier, the number generally increasing with the weight of the suture. Thus, across the range of suture weight (denier) indicated above, the preferred suture of this invention can be constructed with from about 4 up to as many as about 36 individual sheath yarns constructed from individual filaments having the deniers discussed below.

Table I below sets forth broad and preferred ranges for the numbers of sheath yarns which are suitable for the construction of preferred braided sutures of various ranges of overall denier. The pick counts of the sutures vary from about 50 to about 100 and deniers of individual filaments vary from about 0.2 to about 6.0 for the broad range of number of sheath yarns and the pick counts vary from about 55 to about 80 and the deniers of individual filaments vary from about 0.8 to about 3.0, and advantageously from about 1.0 to about 1.8, for the preferred range of number of sheath yarns.

TABLE I

| Sheath Yarns Related to Suture Denier | | | |
|---|---|---|---|
| Overall Suture Denier | Suture Size | Number of Sheath Yarns (Broad Range) | Number of Sheath Yarns (Preferred Range) |
| greater than about 50 to about 125 | 7/0,8/0 | 4-16 | 6-14 |
| greater than about 125 to about 200 | 6/0 | 4-16 | 6-14 |
| greater than about | 5/0 | 4-16 | 6-14 |

TABLE I-continued

Sheath Yarns Related to Suture Denier

| Overall Suture Denier | Suture Size | Number of Sheath Yarns (Broad Range) | Number of Sheath Yarns (Preferred Range) |
|---|---|---|---|
| 200 to about 300 | | | |
| greater than about 300 to about 500 | 4/0 | 10-20 | 12-14 |
| greater than about 500 to about 800 | 3/0 | 14-20 | 14-18 |
| greater than about 800 to about 1200 | 2/0 | 18-32 | 20-30 |
| greater than about 1200 to about 2000 | 0 | 20-36 | 24-34 |
| greater than about 2000 to about 4000 | 1,2 | 20-36 | 24-34 |

While the sheath yarns need not be twisted, it is generally preferred that they be provided with a twist so as to minimize snagging during braid construction.

(4) Individual Filament Denier

The individual filaments comprising each sheath yarn can vary in weight from about 0.2 to about 6.0 denier, preferably from about 0.8 to about 3.0 denier and more preferably from about 1.0 to about 1.8 denier. The number of such filaments present in a particular sheath yarn will depend on the overall denier of the suture as well as the number of sheath yarns utilized in the construction of the suture. Table II sets forth some typical numbers of filaments per sheath yarn for both the broad and preferred ranges of filament weight:

TABLE II

| Number of Filaments per Sheath Yarn | | |
|---|---|---|
| approximate minimum | approximate maximum | Filament Denier |
| 45 | 450 | 0.2 |
| 15 | 150 | 0.5 |
| 5 | 50 | 1.5 |
| 3 | 40 | 1.8 |
| 1 | 15 | 6.0 |

(5) Core (Optional)

For all but the lowest range of overall denier, the preferred suture can optionally be constructed around a filamentous core which itself can be braided or which can be provided in some other configuration such as a twist, ply, cable, etc. The filament(s) comprising the core need not be as fine as those comprising the sheath yarns. It is particularly advantageous for sutures of heavier denier to possess a core. Where a core is provided, it is generally preferred that it possess a weight which is significantly greater than that of a core of a standard suture of equivalent overall denier.

Table III below provides some typical core deniers for sutures of various deniers.

TABLE III

| Overall Suture Denier | Suture Size | Denier of Optional Core (Broad Range) | Denier of Optional Core (Preferred Range) |
|---|---|---|---|
| from about 50 to about 125 | 8/0.7/0 | none | none |
| greater than about 125 to about 200 | 6/0 | 20-80 | 25-50 |
| greater than about 200 to about 300 | 5/0 | 30-100 | 50-80 |
| greater than about 300 to about 500 | 4/0 | 80-50 | 80-120 |
| greater than about 500 to about 800 | 3/0 | 150-300 | 180-280 |
| greater than about 800 to about 1200 | 2/0 | 250-700 | 350-650 |
| greater than about 1200 to about 2000 | 0 | 400-1200 | 500-1000 |
| greater than about 2000 to about 4000 | 1,2 | 800-2400 | 1000-2200 |

When a suture of this invention is fabricated from a material which is susceptible to hydrolysis, e.g., any of the absorbable resins previously mentioned, care must be take to rigorously exclude moisture from contacting the suture during storage or to otherwise preserve the suture from excessive hydrolytic attack which would compromise its in vivo strength to the point where the suture would no longer by serviceable.

Accordingly to U.S. Pat. Nos. 3,728,839 and 4,135,622, the in vivo strength of polyglycolic acid surgical elements such as sutures undergoes significant deterioration on long term storage in the package even on exposure of the contents to very small amounts of water for very short periods of time, e.g., 20 minutes or less, just prior to packaging due to the tendency of a moisture impervious package to seal the moisture in with the suture. To prevent or minimize excessive hydrolytic degradation of an absorbable suture during storage, U.S. Pat. Nos. 3,728,839 and 4,135,622 disclose removing moisture from the suture before sealing the package so that no more than about 0.5 percent of water by weight of suture remains in the package once the package is sealed. This approach to improving the suture's storage stability, while effective, is in practice difficult and expensive to carry out. Prior to sealing the suture within its moisture impervious package, it is essential that the suture be "bone dry", a condition achieved by heating the suture for a sufficient period to remove the water therefrom, e.g., 180°-188° F. (82°-87° C.) for 1 hour under a 26 inch vacuum. However, once the water is removed, the suture cannot be allowed to contact a moisture-containing environment even for a limited duration since as previously noted, even brief exposure to moisture can cause severe deterioration of suture in vivo strength. It therefore becomes necessary following the water removal step to temporarily store the suture in a dry area, i.e., an environment which is essentially free of moisture, where the possibility of contact with moisture is largely eliminated. These operations for improving the storage stability of an absorbable suture are time consuming, expensive and constitute a relatively complex solution to the storage stability problem.

In an entirely different approach to improving the storage stability of an absorbable suture, one that avoids the foregoing drawbacks associated with the method of U.S. Pat. Nos. 3,728,839 and 4,135,622, the storage stability of an absorbable braided suture which is susceptible to hydrolysis is improved by applying to the suture a storage stabilizing amount of at least one water soluble liquid polyhydroxy compound and/or ester thereof. In addition to imparting an enhanced degree of storage stability to the suture, practice of this embodiment of the present invention confers other benefits as well. So, for example, a braided suture which has been filled with a storage stabilizing amount of, e.g., glycerol, exhibits better flexibility and "hand" characteristics than the untreated suture. Moreover, since the polyhydroxy compounds are generally capable of dissolving a variety of medico-surgically useful substances, they can be used as vehicles to deliver such substances to a wound or surgical site at the time the suture is introduced into the body.

The useful storage stabilizing agents are generally selected from the water soluble liquid polyhydroxy compounds and/or esters of such compounds, preferably those having no appreciable toxicity for the body at the levels present. The expression "liquid polyhydroxy compound" contemplates those polyhydroxy compounds which in the essentially pure state are liquids, as opposed to solids, at or about ambient temperature, e.g., at from about 15° C. to about 40° C. The preferred polyhydroxy compounds possess up to about 12 carbon atoms and where the esters are concerned, are preferably the monoesters and diesters.

Among the specific storage stabilizing agents which can be used with generally good results are glycerol and its mono- and diesters derived from low molecular weight carboxylic acids, e.g., monoacetin and diacetin (respectively, glyceryl monoacetate and glyceryl diacetate), ethylene glycol, diethylene glycol, triethylene glycol, 1,3-propanediol, trimethylolethane, trimethylolpropane, pentaerythritol, sorbitol, and the like. Glycerol is especially preferred. Mixtures of storage stabilizing agents, e.g., sorbitol dissolved in glycerol, glycerol combined with monoacetin and/or diacetin, etc., are also useful.

To prevent or minimize run-off or separation of the storage stabilizing agent from the suture, a tendency to which relatively low viscosity compounds such as glycerol are somewhat prone, it can be advantageous to combine the agent with a thickener. Many kinds of pharmaceutically acceptable non-aqueous thickeners can be utilized including water-soluble polysaccharides, e.g., hydroxypropyl methylcellulose (HPMC) and similar cellulosic materials, polysaccharide gums such as guar, xanthan, and the like, gelatin, collagen, etc. An especially preferred class of thickeners are the saturated aliphatic hydroxycarboxylic acids of up to about 6 carbon atoms and the alkali metal and alkaline earth metal salts and hydrates thereof. Within this preferred class of compounds are those of the general formula

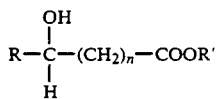

wherein R is hydrogen or a methyl group, R' is hydrogen or a metal selected from the group consisting of alkali metal and alkaline earth metal and n is 0 or 1 and hydrates thereof. Specific examples of such compounds include salts of lactic acid such as calcium lactate and potassium lactate, sodium lactate, salts of glycolic acid such as calcium glycolate, potassium glycolate and sodium glycolate, salts of 3-hydroxy propanoic acid such as the calcium, potassium and sodium salts thereof, salts of 3-hydroxybutanoic acid such as the calcium, potassium and sodium salts thereof, and the like. As stated hereinbefore, hydrates of these compounds can also be used. Calcium lactate, especially calcium lactate pentahydrate, is a particularly preferred thickener.

Where a thickener is utilized, it will be incorporated in the storage stabilizing composition in at least that amount required to increase the overall viscosity of the composition to the point where it no longer readily drains away from the suture in a relatively short period. In the case of a preferred storage stabilizing agent-thickener combination, namely, glycerol and calcium lactate, the weight ratio of glycerol to calcium lactate can vary from about 1:1 to about 10:1 and preferably is from about 6:1 to about 8:1.

If necessary or desirable, the storage stabilizing agent together with optional thickener can be dissolved in any suitable non-aqueous solvent or combination of solvents prior to use. To be suitable, the solvent must (1) be miscible with the storage stabilizing agent and optional thickener, (2) have a sufficiently high vapor pressure to be readily removed by evaporation, (3) not appreciably affect the integrity of the suture and (4) be capable of wetting the surface of the suture. Applying these criteria to a preferred storage stabilizing agent, glycerol, advantageously in admixture with a preferred thickener, calcium lactate, lower alcohols such as methanol and ethanol are entirely suitable solvent carriers. When a solvent is utilized in the preparation of the storage stabilizing agent, such solvents, e.g., methanol, can be employed in amounts providing a solution concentration of from about 20% to about 50%, preferably about 304 to about 454, by weight of the storage stabilizing agent (including any optional thickener) based on the total weight of the solution.

Preparing the storage stabilizing agent for application to the suture is a relatively simple procedure. For example, in the case of a mixture of glycerol and calcium lactate, the desired amount of glycerol is first introduced to a suitable vessel followed by the addition thereto of the desired amount of calcium lactate. If no solvent is used, the mixture is then thoroughly mixed. Where a solvent such as methanol is employed, the solvent is added to the mixture of glycerol and calcium lactate and the solution is then thoroughly mixed to dissolve the compounds.

Application of the storage stabilizing agent to the suture can be carried out in any number of ways. Thus, for example, the suture can be submerged in the storage stabilizing agent or solution thereof until at least a storage stabilizing amount of agent is acquired or otherwise retained by the suture, even after the optional removal of any excess agent and/or accompanying solvent (if present) such as by drainage, wiping, evaporation, etc. In many cases, contact times on the order of from just a few seconds, e.g., about 10 seconds or so, to several hours, e.g., about 2 hours and even longer, are sufficient to impart a substantial improvement in the storage stability of the treated suture compared to the same suture which has not been treated with storage stabilizing agent. It has been found that calendering the suture prior to filling, such as by passing the suture through at least two pairs of transversely mounted calender rolls, can improve the receptivity of the suture to filling and improves the suppleness of the resulting filled suture. It is believed that calendering the suture separates the individual suture filaments to open up spaces therebetween which are conducive to ensuring that the filling composition penetrates within, and fills, the interstices of the braided suture.

The foregoing submersion method of contacting the suture with storage stabilizing agent can be conducted continuously or in batch. Thus, a running length of the suture can be continuously passed through a quantity of the stabilizing agent at a velocity which has been previously determined to provide the necessary degree of exposure, or contact time, of the suture with the storage stabilizing agent. As the suture emerges from the storage stabilizing agent, it can be passed through a wiper or similar device to remove excess agent prior to the packaging operation. Preferably, the suture is passed through a coating head supplied by a metering pump with a constant supply of filling solution, with the suture emerging from the coating head and passing through an evaporation oven to remove the filling solution solvent prior to any further surface contact, i.e., with rollers, etc. In a batch operation, a quantity of suture is rarely submerged within the storage stabilizing agent for the requisite period of time with any excess agent being removed from the suture if desired.

Alternatively, the storage stabilizing agent and solutions thereof can be applied to the suture by spraying, brushing, wiping, etc., such that the suture receives and retains at least a storage stabilizing amount of the agent. Yet another procedure which can be used to apply the storage stabilizing agent involves inserting the suture in a package containing an effective amount of the agent such that intimate contact between the suture and the agent is achieved.

Whatever the contacting procedure employed, it is necessary that the suture being treated acquire a storage stabilizing amount of the storage stabilizing agent. In general, amounts of from about 2 to about 25, and preferably from about 5 to about 15 weight percent, of storage stabilizing agent(s) (exclusive of any solvent) by weight of the suture contacted therewith is sufficient to provide significantly improved storage stability compared to that of the untreated suture.

As previously pointed out, a filled braided suture in accordance with the invention need not be packaged and maintained under the very dry conditions required for prior synthetic absorbable sutures. Instead, it is preferred that the filled sutures be equilibrated so that the level of moisture or other stabilizing agent solvent is sufficient to result in an appropriate viscosity level for the stabilizing agent and thickener in order to keep the stabilizing agent on the suture. In the preferred embodiment of a braided suture filled with a mixture of glycerol and calcium lactate, the moisture level may be equilibrated to as low as about 0.2% by weight of the suture, and is preferably above 0.3% or, even more preferably, about 0.5% by weight of the suture.

Indeed, it has been found that a braided suture filled with a glycerol/calcium lactate composition tends to undergo undesirable changes if exposed to a very dry environment. More particularly, if such a filled suture is exposed to a very dry environment, the surface of the suture may accumulate a flaked or powdered substance which could possibly interfere with, or render more difficult, the removal of the suture from its package. Equilibrating the filled suture, such as in a dew point controlled environment, so that the suture contains a relatively high moisture level, e.g., in excess of 0.2% and preferably in excess of 0.5% by weight of the suture, prevents such accumulation of flaked or powdered substance which might otherwise result were the suture exposed to an extremely dry environment. Conversely, the presence of too much moisture can also have deleterious effects, such as causing the glycerol filling to run. Therefore, it is preferable to control the moisture level within a range having preset upper and lower limits.

It is also within the scope of this invention to impregnate the braided suture with, or otherwise apply thereto, one or more medico-surgically useful substances, e.g., those which accelerate or beneficially modify the healing process when the suture is applied to a wound or surgical site. So, for example, the suture herein can be provided with a therapeutic agent which will be deposited at the sutured site. The therapeutic agent can be chosen for its antimicrobial properties, capability for promoting wound repair and/or tissue growth or for specific indications such as thrombosis. Antimicrobial agents such as broad spectrum antibiotics (gentamicin sulphate, erythromycin or derivatized glycopeptides) which are slowly released into the tissue can be applied in this manner to aid in combating clinical and sub-clinical infections in a surgical or trauma wound site.

To promote wound repair and/or tissue growth, one or more biologically active materials known to achieve either or both of these objectives can be applied to the spiroid braided suture of the present invention. Such materials include any of several Human Growth Factors (HGFs), magainin, tissue or kidney plasminogen activator to cause thrombosis, superoxide dismutase to scavenge tissue damaging free radicals, tumor necrosis factor for cancer therapy, colony stimulating factor, interferon, interleukin-2 or other lymphokine to enhance the immune system, and so forth.

The term "Human Growth Factor" or "HGF" embraces those materials, known in the literature, which are referred to as such and includes their biologically active closely related derivatives. The HGFs can be derived from naturally occurring sources including human and non-human sources, e.g., bovine sources, and are preferably produced by recombinant DNA techniques. Specifically, any of the HGFs which are mitogenically active and as such are effective in stimulating, accelerating, potentiating or otherwise enhancing the wound healing process can be usefully applied to the suture herein, e.g., HEGF (urogastrone), TGF-beta, IGF, PDGD, FGF, etc. These and other useful HGFs and closely related HGF derivatives, methods by which they can be obtained and methods and compositions featuring the use of HGFs to enhance wound healing are variously disclosed, inter alia, in U.S. Pat. Nos. 3,883,497, 3,917,824, 3,948,875, 4,338,397, 4,418,691, 4,528,186, 4,621,052, 4,743,679, 4,717,717, 4,861,757, 4,874,746 and 4,944,948, European Patent Application Nos. 046,039, 128,733, 131,868, 136,490, 147,178, 150,572, 177,915 and 267,015, PCT International Applications WO 83/04030, WO 85/003698, WO 85/01284 and WO 86/02271, UK Patent Applications GB 2 092 155 A, 2 162 851 A and GB 2 172 890 A and, "Growth Factors in Wound Healing", Lynch, et al., *J. Clin. Invest.*, Vol. 84, pages 640–646 (August 1989), all of which are incorporated by reference herein. Of the known HGFS, HEGF, TGF-beta, IGF, PDGF and FGF are preferred, either singly or in combination.

In a preferred embodiment of the braided suture device of this invention, a filling composition comprising a surgical wound healing enhancing amount of at least one HGF and as carrier therefor at least one water soluble, liquid polyhydroxy compound and/or ester thereof such as any of those previously mentioned is applied to the suture. The carrier protects the HGF component of the filling composition from excessive degradation or loss of biopotency during storage and as disclosed above, when the suture is fabricated from an absorbable resin which is susceptible to hydrolysis, the carrier improves the storage stability of the suture as well. In addition to carrier, the HGF can contain a thickener such as any of those previously mentioned in order to reduce or limit the tendency of carrier run-off.

The filling composition can contain one or more additional components which promote or enhance the wound healing effectiveness of the HGF component. Thus, e.g., site-specific hybrid proteins can be incorporated in the filling composition to maximize the availability of the HGF at the wound site and/or to potentiate wound healing. See, e.g., Tomlinson (Ciba-Geigy Pharmaceuticals, West Sussex, U.K.), "Selective Delivery and Targeting of Therapeutic Proteins", a paper presented at a symposium held June 12–14, 1989 in Boston, Mass., the contents of which are incorporated by reference herein. The HGFs can also be associated with carrier proteins (CPs), e.g., in the form of CP-bound HGF(s), to further enhance availability of the HGF(S) at a wound site as disclosed in "Carrier Protein-Based Delivery of Protein Pharmaceuticals", a paper of BioGrowth, Inc., Richmond, Calif. presented at the aforementioned symposium, the contents of said paper being incorporated by reference herein. The HGFs can also be incorporated in liposomes to provide for their release over an extended period. Lactate ion can be present to augment the wound healing activity of the HGF. Protectants for the HGF can also be utilized, e.g., polyethylene glycols, acetoxyphenoxy polyethoxy ethanols, polyoxyethylene sorbitans, dextrans, albumin, poly-D-alanyl peptides and N-(2-hydroxypropyl)-methacrylamide (HPMA).

The amounts of HGF, carrier and optional component(s) such as thickener, site-specific hybrid protein, carrier protein, etc., identified above can vary widely and in general will be at least that amount of a particular component which is required to perform its respective function in an effective way. Those skilled in the art employing known or conventional procedures can readily determine optimum amounts of each component for a particular filling composition and particular braided suture filled therewith.

In general, the HGF(S) can be present in the total composition at a level ranging from about 0.1 to about 25,000 micrograins per gram of such composition, preferably from about 0.5 to about 10000 micrograms per gram of composition and most preferably from about 1 to about 500 micrograms per gram of composition.

Application of the HGF-containing composition to the suture can be carried out by any suitable technique, e.g., by any of the procedures described above for applying a storage stabilizing agent to the suture.

It can also be advantageous to apply one or more coating compositions to the suture where particular functional properties are desired. For example, the suture can be coated with a material which improves its surface lubricity and/or knot tie-down characteristics. Materials of this kind are known, e.g., those described in U.S. Pat. Nos. 3,942,532, 40406,533 and 4,716,203, the contents of which are incorporated by reference herein. Particularly suitable materials which impart either or both improved lubricity and knot-tie down characteristics are the bioabsorbable coating compositions obtained by copolymerizing in accordance with known procedures (1) a polyether glycol selected from the group consisting of relatively low molecular weight polyalkylene glycol, e.g., one corresponding to the general formula $HO(RO)_yH$ wherein R is an alkylene group of from 2–4 carbon atoms and y is an integer of from about 100–350, and polyethylene oxide-polypropylene oxide block copolymer, e.g., one corresponding to the general formula $H(OCH_2CH_2)_x(OC_3H_6)_y(OCH_2CH_2)_zOH$ wherein x is an integer of from about 45–90, y is an integer of from about 60–85 and z is an integer of from about 45–90 with (2) a mixture of lactide monomer and glycolide monomer or a preformed copolymer of lactide and glycolide, the weight ratio of (1) to (2) preferably ranging from about 4:1 to about 1:4 and more preferably from about 2:1 to about 1:2. The ratio of lactide to glycolide in the monomer mixture or in the copolymer of these monomers preferably varies from about 65–90 mole percent lactide and 10–35 mole percent glycolide. Polyether glycols which can be used to prepare the bioabsorbable coating compositions advantageously include polyethylene glycols having molecular weights of about 3,500–25,000 and preferably from about 4,000–10,000 and polyethylene oxide-polypropylene oxide block copolymers having molecular weights of from about 5,000–10,000 and preferably from about 7,500 to about 9,000, e.g., those disclosed in U.S. Pat. Nos. 2,674,619, 3,036,118, 4,043,344 and 4,047,533 and commercially available as the Pluronics (BASF-Wyandotte). Where preformed copolymers of lactide and glycolide are employed in preparing the bioabsorbable coating compositions, they may be prepared as described in U.S. Pat. No. 4,523,591. The amounts of bioabsorbable coating composition to be applied to the suture, e.g., by coating, dipping, spraying or other appropriate technique will vary depending upon the specific construction of the suture, its size and the material of its construction. In general, the coating composition applied to an unfilled suture will constitute from about 1.0 to about 3.0 percent by weight of the coated suture, but the amount of coating add on may range from as little as about 0.5 percent, by weight, to as much as 4.0 percent or higher. For a preferred filled (i.e. containing a storage stabilizing agent) braided suture, amounts of coating composition will generally vary from about 0.5% to 2.0% with as little as 0.2% to as much as 3.0%. As a practical matter and for reasons of economy and general performance, it is generally preferred to apply the minimum amount of coating composition consistent with good surface lubricity and/or knot tie-down characteristics and this level of coating add on is readily determined experimentally for any particular suture.

The following examples are illustrative of the braided suture of this invention.

Comparison Examples 1–7

The following braided suture configurations are disclosed in U.S. Pat. No. 3,565,077:

| Comparison Example | Overall Suture Denier | Pick Count | Number of Sheath Yarns | Denier of Individual Filaments | Denier of Core |
| --- | --- | --- | --- | --- | --- |
| 1 | 175 | 40 | 6 | 6 | 25 |
| 2 | 300 | 46 | 8 | 6 | 100 |
| 3 | 500 | 40 | 8 | 6 | 100 |
| 4 | 800 | 50 | 12 | 6 | 200 |
| 5 | 1200 | 50 | 16 | 6 | 400 |
| 6 | 1500 | 50 | 12 | 6 | 600 |

-continued

| Comparison Example | Overall Suture Denier | Pick Count | Number of Sheath Yarns | Denier of Individual Filaments | Denier of Core |
|---|---|---|---|---|---|
| 7 | 2000 | 40 | 16 | 6 | 800 |

Sutures possessing approximately these configurations are relatively inflexible, rough-surfaced and exhibit a relatively high level of chatter and drag.

Comparison Examples 8-11

The following braided suture configurations are those of four commercially available sutures:

| Comparison Example | Overall Suture Denier | Suture Size | Pick Count | Number of Sheath Yarns | Denier of Individual Filaments | Denier of Core |
|---|---|---|---|---|---|---|
| 8 | 259 | 5/0 | 47 | 8 | 2.1 | 29 |
| 9 | 698 | 3/0 | 52 | 12 | 2.1 | 55 |
| 10 | 1566 | 0 | 50 | 16 | 2.1 | 252 |
| 11 | 2122 | 1 | 44 | 16 | 2.2 | 330 |

Photomicrographs obtained by scanning electron microscopy (SEM) of the suture of Comparison Example 10 (FIGS. 4 and 5: cross-sectional view at 200× and linear view at 5×, respectively) clearly show the structural details of the suture. The suture braid is made up of relatively few sheath yarns and the circumferential indentations, plainly evident in FIG. 4, cause the braid surface to be relatively rough.

Examples 1-8

These examples illustrate various sizes of braided suture constructed in accordance with the present invention.

| Example | Overall Suture Denier | Suture Size | Pick Count | Number of Sheath Yarns | Denier of Individual Filaments | Denier of Core |
|---|---|---|---|---|---|---|
| 1 | 96 | 7/0 | 82 | 8 | 1.2 | — |
| 2 | 173 | 6/0 | 75 | 12 | 1.2 | 29 |
| 3 | 240 | 5/0 | 65 | 8 | 1.2 | 48 |
| 4 | 389 | 4/0 | 75 | 12 | 1.2 | 101 |
| 5 | 600 | 3/0 | 65 | 16 | 1.2 | 216 |
| 6 | 1080 | 2/0 | 72 | 24 | 1.2 | 504 |
| 7 | 1378 | 0 | 65 | 28 | 1.2 | 706 |
| 8 | 2028 | 1 | 65 | 32 | 1.2 | 1260 |

Comparing the details of construction of the foregoing braided sutures with those of the known braided sutures as set forth in Comparison Examples 1-11, it will be noted that for sutures of comparable overall denier, the suture of this invention possesses a significantly greater pick count and number of sheath yarns and a significantly finer denier for the individual filaments making up a sheath yarn than the equivalent characteristics of the known suture.

As a result of their unique construction characteristics, the suture of this invention exhibits perceptibly improved flexibility and hand and reduced chatter and drag compared with the known, or standard, sutures of Comparison Examples 1-11. For a given suture size, a braided suture of this invention will typically exhibit a level of tissue drag not exceeding about 60%, preferably not exceeding about 404 and more preferably, not exceeding about 20%, of the tissue drag of a standard braided suture of comparable size.

Examples 9-12

The following braided sutures were fabricated in accordance with the present invention:

| Example | Overall Suture Denier | Suture Size | Pick Count | Number of Sheath Yarns | Denier of Individual Filaments | Denier of Core |
|---|---|---|---|---|---|---|
| 9 | 240 | 5/0 | 68 | 8 | 1.2 | 40 |
| 10 | 600 | 3/0 | 71 | 16 | 1.2 | 180 |
| 11 | 1374 | 0 | 67 | 28 | 1.2 | 702 |
| 12 | 2230 | 1 | 57 | 32 | 1.2 | 975 |

In contrast to the suture of Comparison Example 10, supra, SEM photomicrographs of the suture of Example 11 (FIGS. 6 and 7: cross-sectional view at 20× and linear view at 50×, respectively) show a smooth circumferential surface as the result of the increased number of sheath yarns and smaller diameter of individual filaments.

Figure 4:
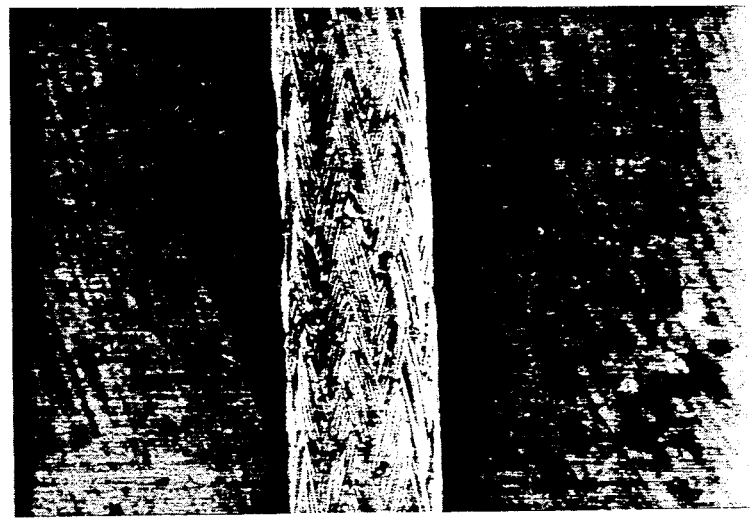
Figure 6:
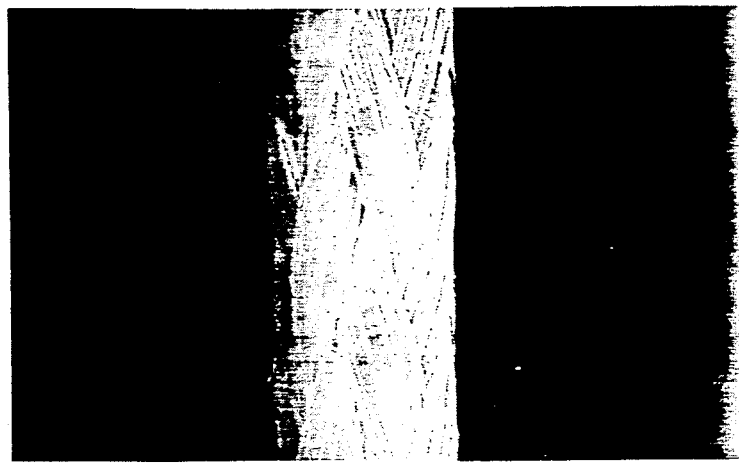

FIG. 4 as compared to FIG. 6 shows the relatively larger core present in the suture of Example 11 as compared to that of Comparison Example 10.

Figure 5:
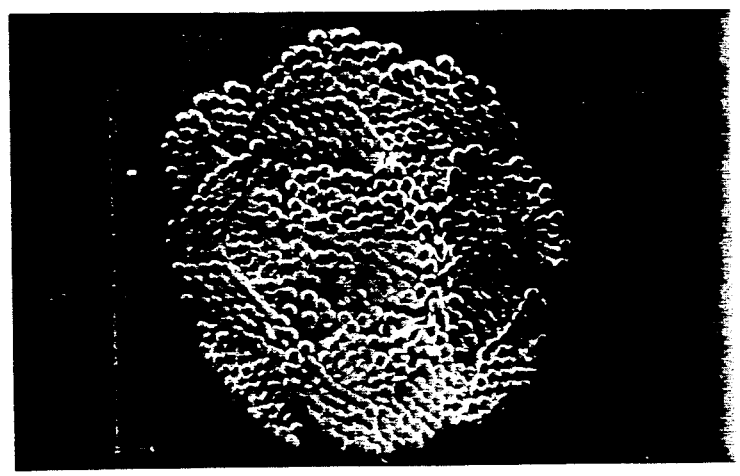
Figure 7:
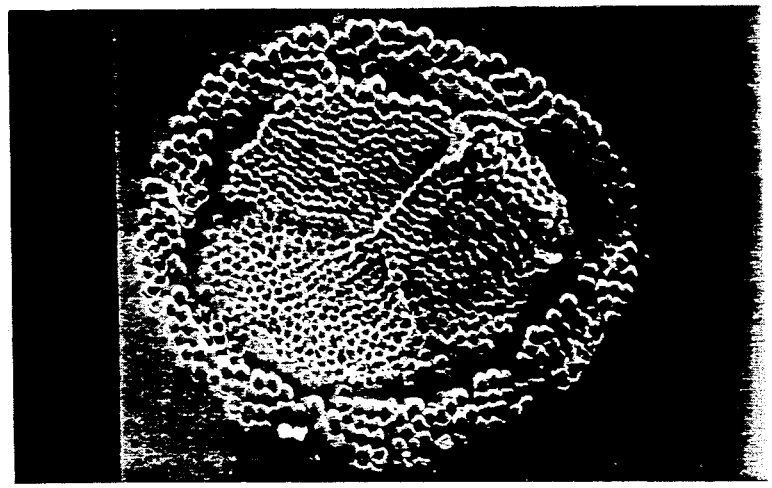

Comparison between FIGS. 5 and 7 shows the increased number of picks (crossovers/inch) of the suture of Example 11 as compared to that of Comparison Example 10.

EXAMPLES 13-15

The following suture braids were fabricated in accordance with the present invention:

| Example | Overall Suture Denier | Suture Size | Pick Count | Number of Sheath Yarns | Denier of Individual Filaments | Denier of Core |
|---|---|---|---|---|---|---|
| 13 | 1442 | 0 | 70 | 28 | 2.0[1] | 882 |
| 14 | 1621 | 0 | 70 | 28 | 1.2 | 882 |
| 15 | 1554 | 0 | 78 | 28 | 1.2 | 882 |

The suture braids were coated to improve suture lubricity and knot tie-down characteristics and compared for physical properties for diameter USP knot-pull and suture tissue drag with the coated commercial suture of Comparison Example 10.

In this tissue drag test, sutures were needled with identical tapered needles to normalize any effect of needle diameter on the test.

Sutures were passed through live animal abdominal fascia tissue. The results of the tissue drag study are shown in Table IV as follows:

TABLE IV

| | Tissue Drag Results | | |
|---|---|---|---|
| Example | Diameter (min) | Knot-Pull (Kg) | Tissue Drag (gms force, maximum) |
| Comparison Example 10 | 0.419 | 4.72 | 257 |
| 13 | 0.413 | 5.27 | 35 |
| 14 | 0.428 | 5.35 | 56 |
| 15 | 0.444 | 5.04 | 50 |

Figure 8:
Figure 9:
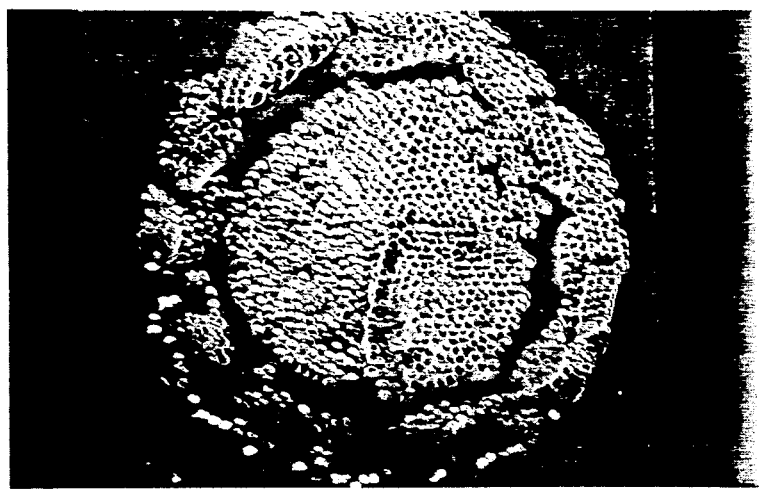
Figure 10:
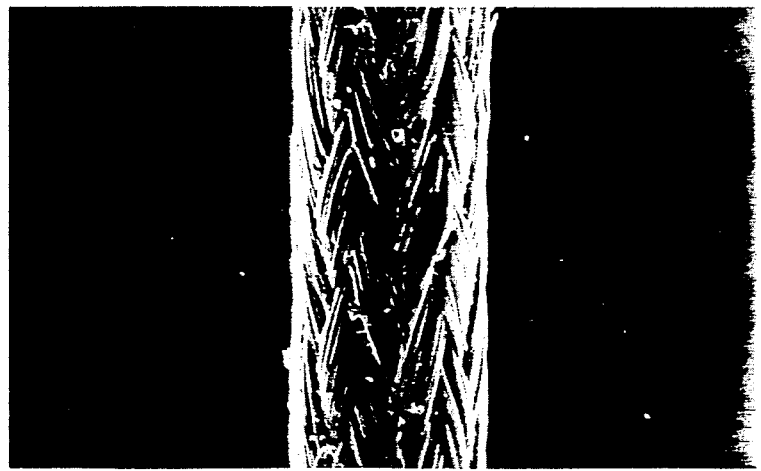
Figure 11:
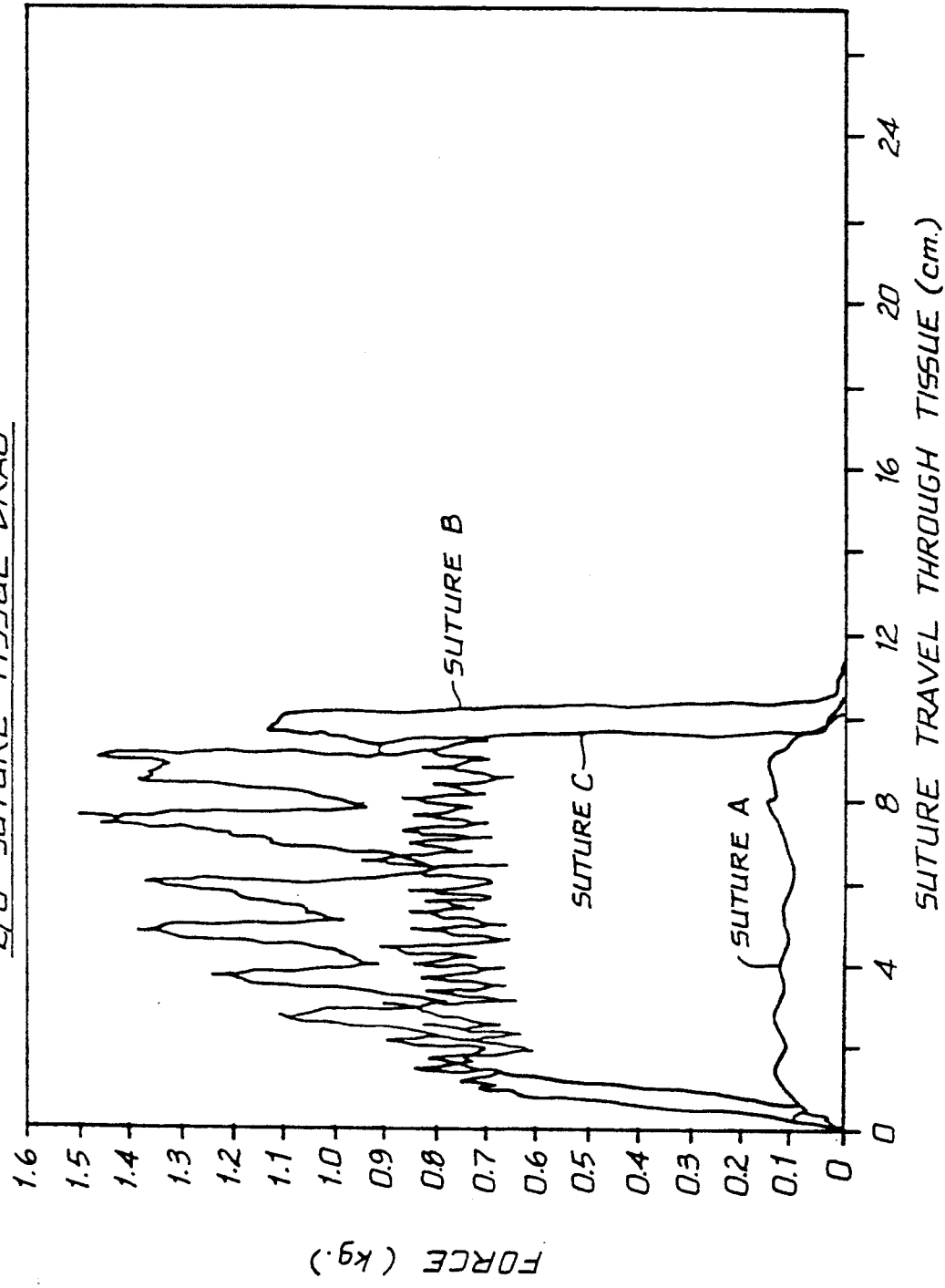
FIGS. 11-16 are graphical comparisons of the measured tissue drag performance of braided sutures of this invention compared with that of standard sutures of substantially equivalent size; and, FIGS. 17A-17C illustrate the formation of the knot which was employed in the knot security measurement test of Examples 22-31, infra.
Figure 12:
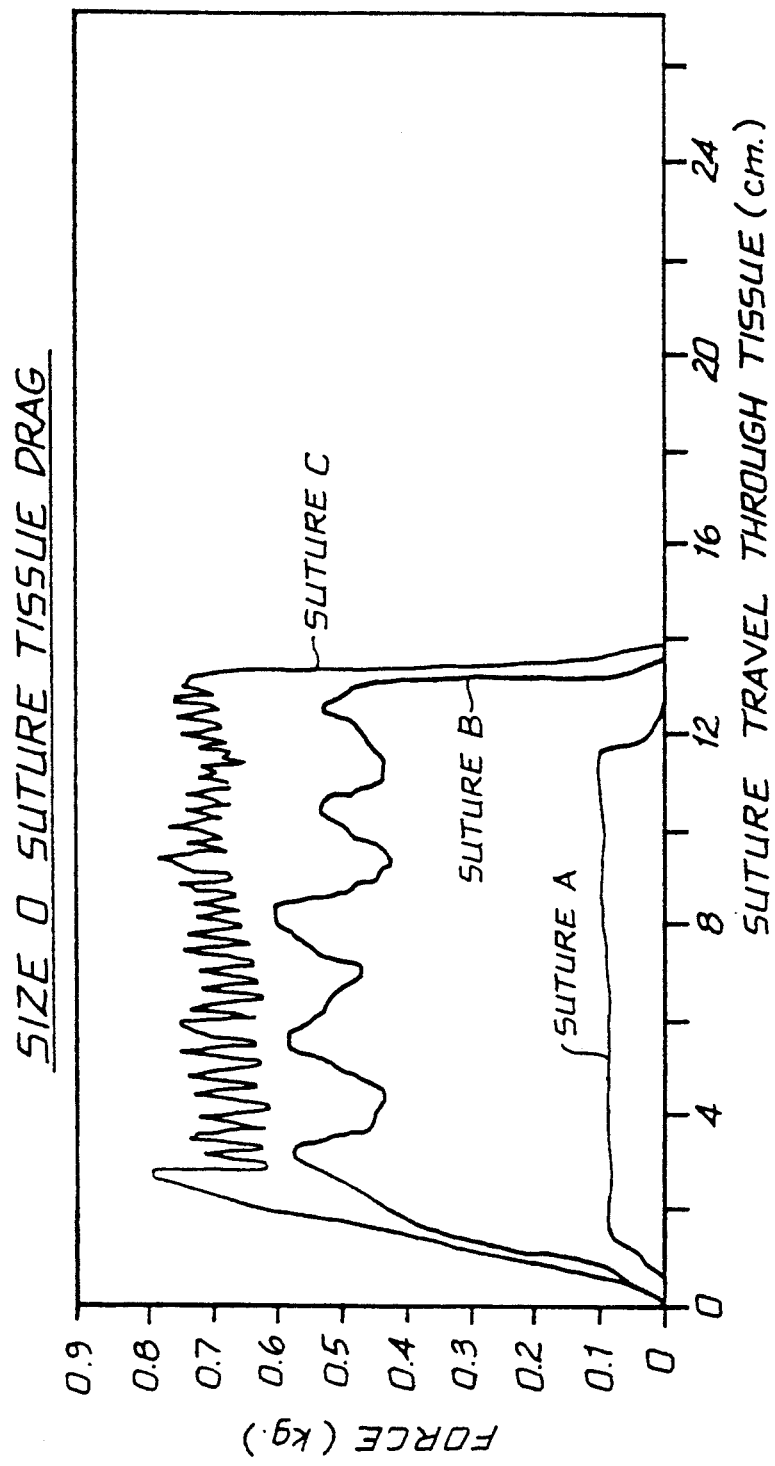
Figure 13:
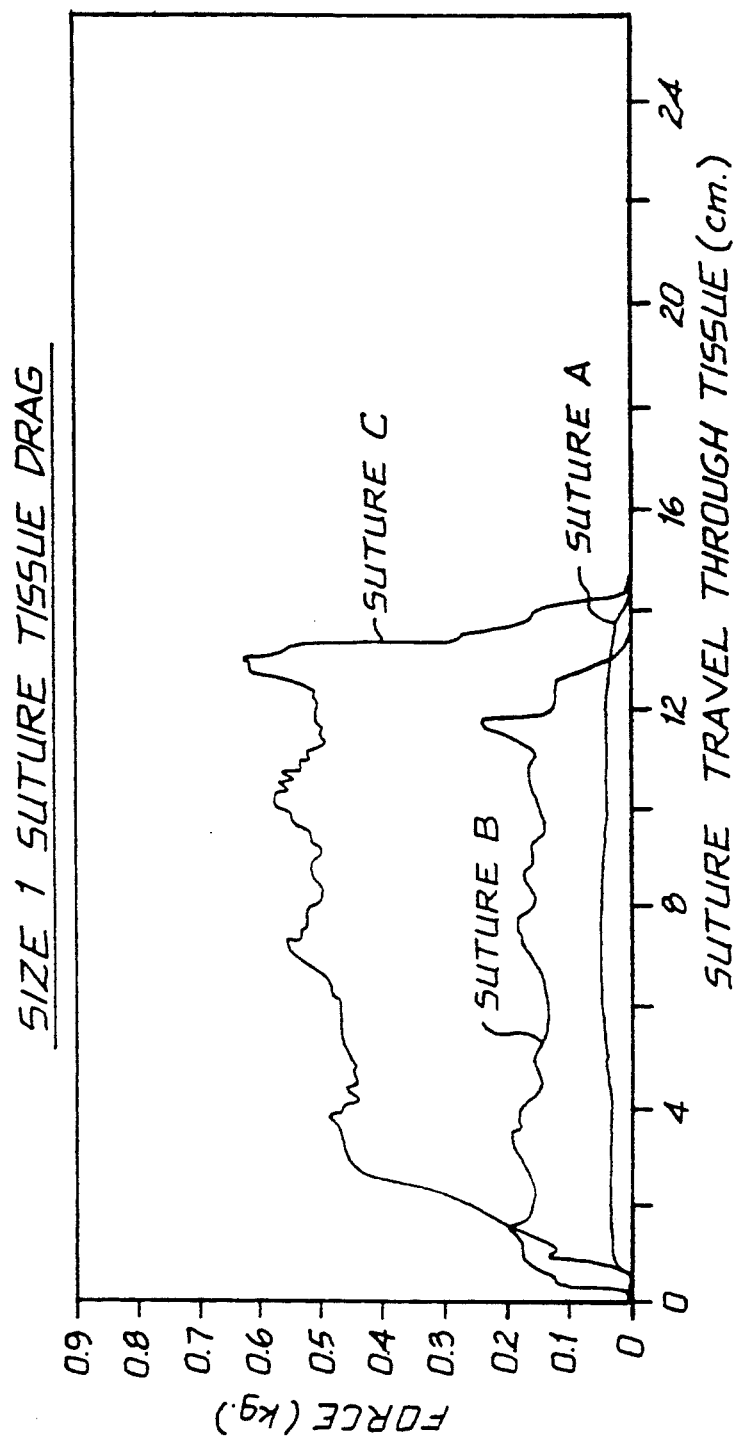
Figure 14:
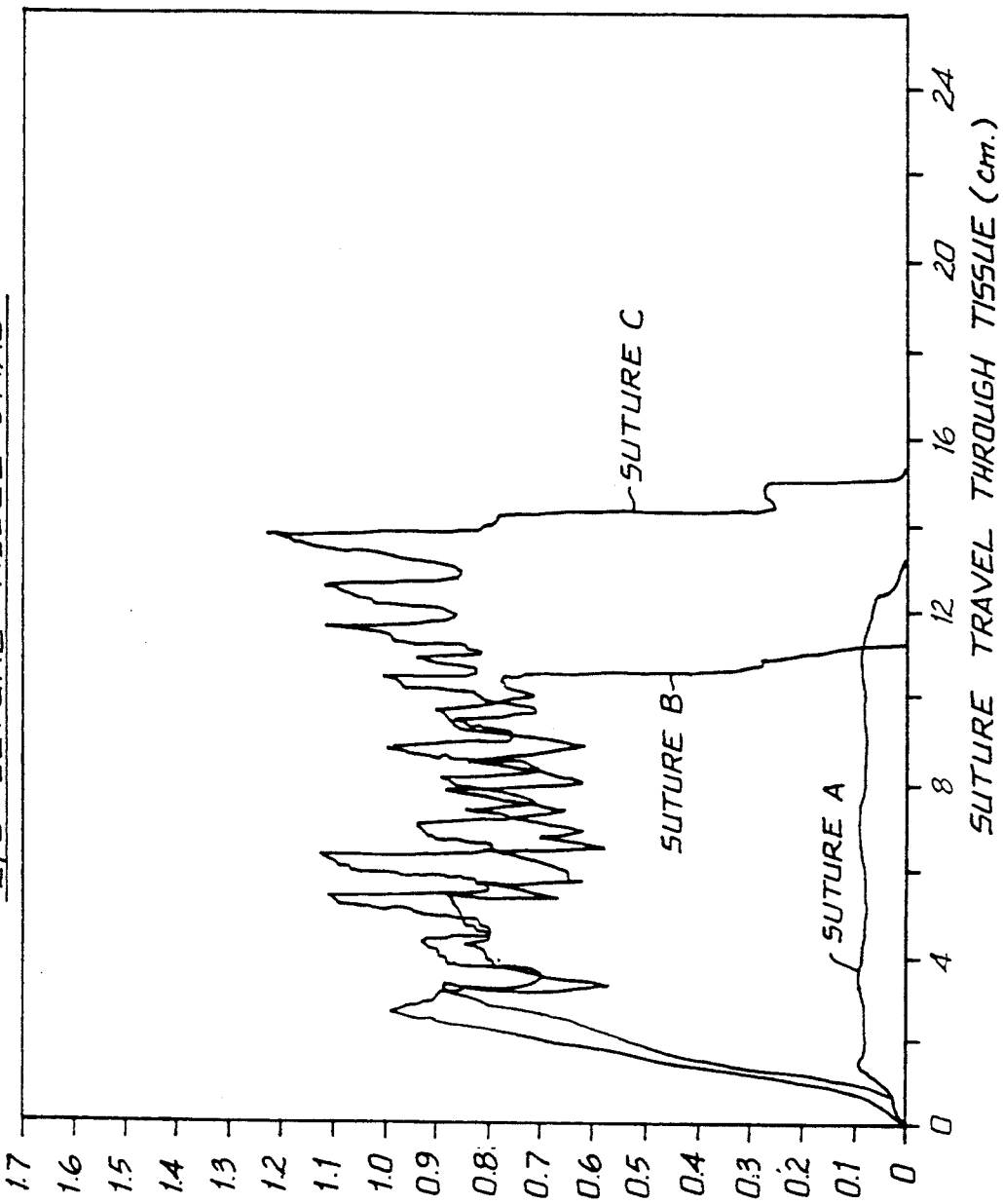
Figure 15:
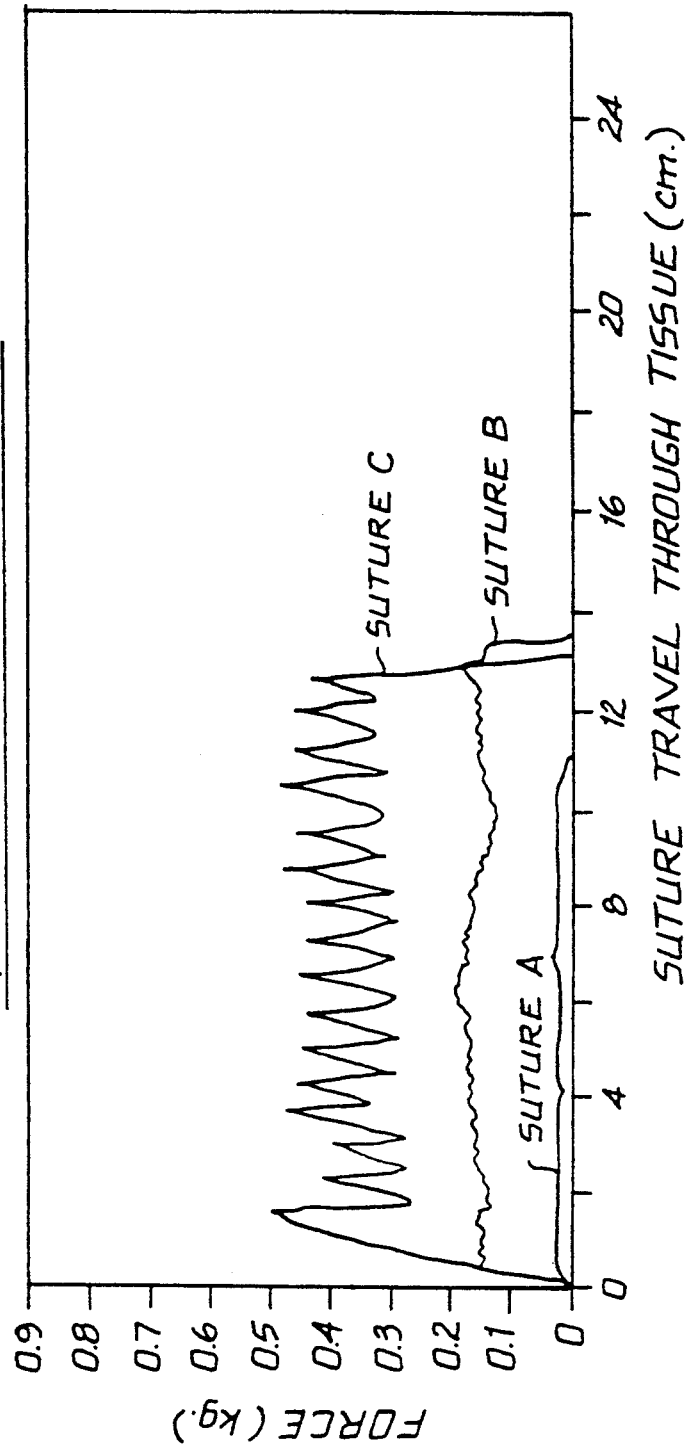
Figure 16:
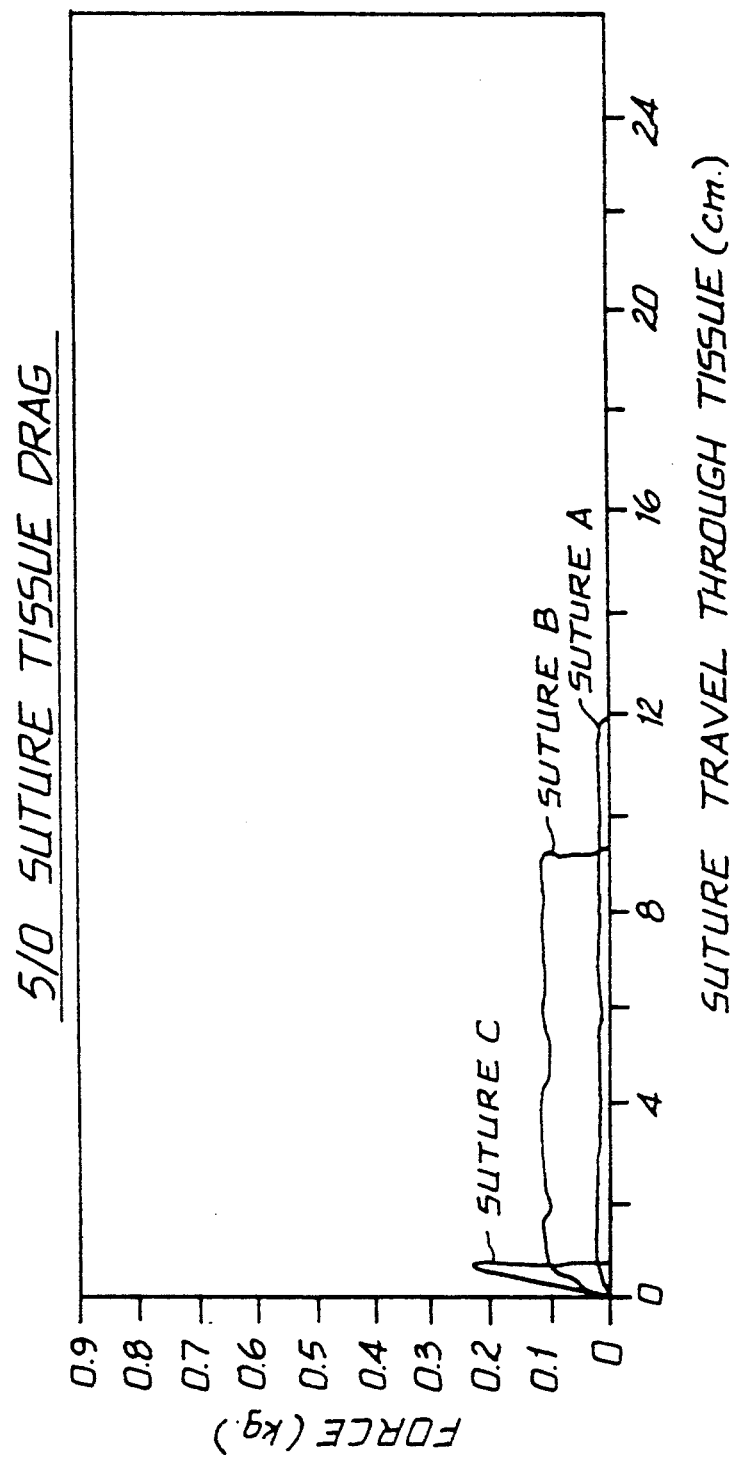

These data clearly show that the smoother surface of the braided sutures fabricated in accordance with this invention provides smoother, more resistance-free passage of the suture through tissue thereby resulting in lower tissue drag and chatter. High drag forces make it more difficult for the surgeon to align tissue neatly and increase the time to complete the closure. A visual comparison of the suture of comparative Example 10 and those of Examples 13 and 14 of this invention are consistent with the tissue drag observations set forth above. Thus, it is evident from a visual comparison of the SEM photomicrographs of FIGS. 8 and 9 (suture of Comparison Example 10 shown in cross-sectional view at 150× and linear view at 70×, respectively) with those of FIGS. 10 and 11 (suture of Example 13 shown in cross-section at 150× and linear view at 70×, respectively) and FIGS. 12 and 13 (suture of Example 14 shown in cross-section at 150× and linear view at 70×, respectively) that the external surfaces of the sutures of the present invention, i.e., those of Examples 13 and 14, are perceptibly smoother than the surfaces of the suture of Comparison Example 10.

EXAMPLE 16

Measurement of tissue drag in accordance with this example employed a Chatillon Tensile Tester (serial no. 06279-1) equipped with a load cell (Full Scale Load 1.72 g) for recording tensile and compression loads, a stripchart recorder (Onega Eng. serial no. 211347) for constantly recording the tensile loads and crosshead movement, a 500 gram calibration weight and needle holders (Miltex Straight-6").

Each suture sample which was tested was armed with the same needle (for size and type) to reduce the potential for error resulting from varying punctures by different needles. For each test, the armed suture was passed through the fascia tissue in a "W" pattern thus assuring that an approximately 1 inch spacing would be maintained between entries and exits of the suture. In each passage of the suture, care was taken to insure entry of the suture into all fascia layers (excluding the skin). Following passage of an adequate length of suture through the fascia tissue to accommodate the test setup, the needle was placed into needle holders. The suture was passed under a ringstand bar creating a 90° angle directly aligned with the load cell and the specimen. The needle holder was suspended from the load cell fixture. Tension in the suture was relieved and the zero settings on the tensile tester were rechecked prior to testing.

The crosshead was then engaged in the test direction (tensile, upward) at a rate of 30 cm/min (12 in/min) and the stripchart recorder was manually engaged at a rate of 30 cm/min (12 in/min). During the testing of the suture, load and crosshead movement were recorded until the entire suture sample had been withdrawn from the tissue or complete crosshead travel had been achieved. The crosshead was then disengaged and returned to its zero setting, the stripchart was disengaged and any remaining length of suture was removed from the fascia.

The foregoing procedure was repeated for each armed suture within a test group.

In this example, a filled and coated size 2/0 braided suture constructed in accordance with the invention (Suture A) was compared with a coated size 2/0 braided silk suture of Davis & Geck, Inc. ("D & G Silk": Suture B) and a coated size 2/0 braided absorbable suture of Ethicon, Inc. ("Vicryl": Suture C) for tissue drag as described. The tissue drag profiles of the three sutures appear in FIG. 11 as the plot of force (kg) required to pull each suture through animal fascia tissue through a distance of somewhat greater than 10 cm. As the graphically represented data show, the braided suture constructed in accordance with the principles of this invention, i.e., Exhibit A, exhibited a dramatically reduced level of tissue drag compared with that of the two standard sutures, i.e., Sutures B and C.

EXAMPLES 17-21

Example 16 was repeated with different sizes of Sutures A, B and C, namely, sizes 0 (Example 17), 1 (Example 18), 2/0 (Example 19), 4/0 (Example 20) and 5/0 (Example 21). As shown in FIGS. 12-16, each size of Suture A exhibited far lower tissue drag than standard Sutures B and C of substantially equivalent size.

EXAMPLES 22-31

Figure 17A:
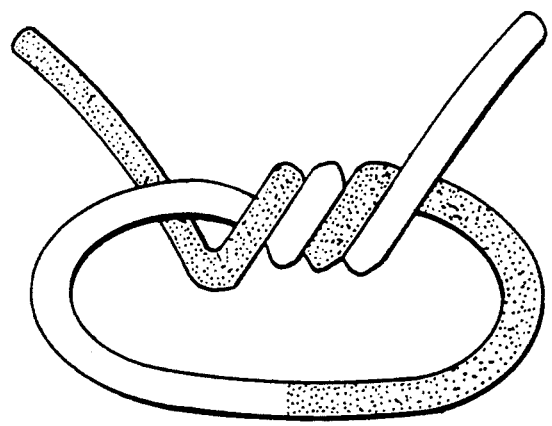
Figure 17B:
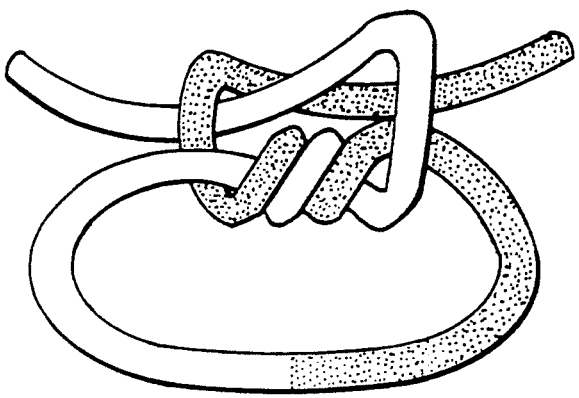
Figure 17C:
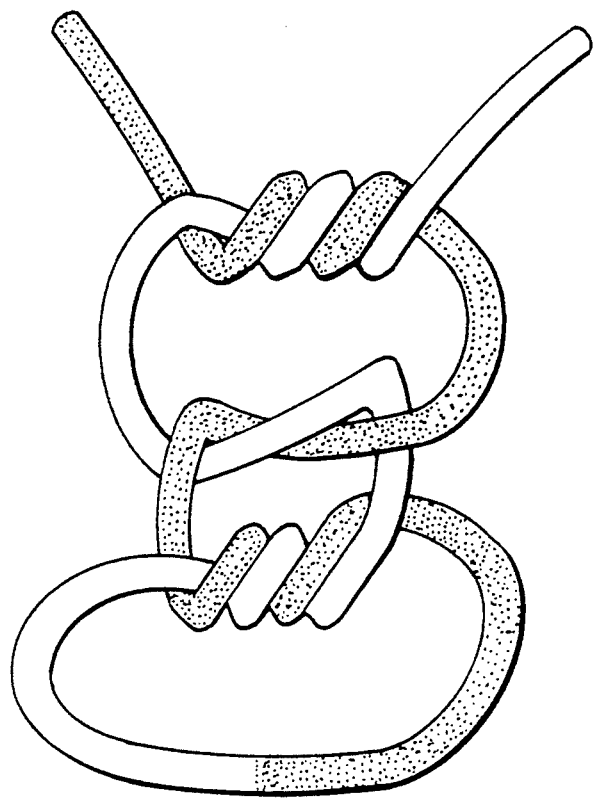

Knot security was measured in terms of the amount of force which, when applied to a loop possessing the knot shown in FIGS. 17A-17C, causes the knot to slip or the loop to break.

The details of the knot security test are as follows:

Each suture in the test set was approximately 7 inches in length. A knotted loop was formed in a test suture in three steps as illustrated in FIGS. 17A-17C. As shown in Step 1 of 17A, each suture was given a double throw (left over right) around a 2 cm diameter cylinder. In Step 2, the free ends of the suture were set with a single throw (right over left) onto the initial throw of Step 1. Finally, in Step 3, another double throw (left over right) was set onto the single throw of Step 2 to complete the knot. The free ends of the suture were cut to approximately ½ inch and the loop was carefully eased from the cylinder.

Testing of each loop was carried out employing a calibrated Instron machine operated in a conventional manner. For each size suture, up to 20 test samples were prepared and measured for loop pull strength. The test results for all of the sutures in all sizes are set forth in Table V as follows:

TABLE V

Knot Security of Bioabsorbable Sutures Measured As Loop Pull Strength (kg)

Example 22: Size 1
Suture of this Invention

| Test | Gage Reading (kg) | Broken Loop (B) or Slippage of Knot (S) |
|---|---|---|
| 1 | 13.5 | B |
| 2 | 13.8 | B |
| 3 | 14.1 | B |
| 4 | 14.8 | B |
| 5 | 13.9 | B |
| 6 | 13.9 | B |
| 7 | 13.4 | B |
| 8 | 13.2 | B |
| 9 | 13.3 | B |
| 10 | 13.2 | B |
| 11 | 13.6 | B |
| 12 | 13.2 | B |
| 13 | 14.3 | B |
| 14 | 13.8 | B |
| 15 | 13.6 | B |
| 16 | 14.0 | B |
| 17 | 14.3 | B |
| 18 | 14.2 | B |
| 19 | 14.0 | B |
| 20 | 13.3 | B |

Example 23: Size 2

| Standard Suture | | Suture of this Invention | |
|---|---|---|---|
| Gage Reading | Broken Loop (B) or Slippage | Gage Reading | Broken Loop (B) or Slippage |

TABLE V-continued

Knot Security of Bioabsorbable Sutures Measured As Loop Pull Strength (kg)

| Test | (kg) | of Knot (S) | (kg) | of Knot (S) |
|---|---|---|---|---|
| 1 | 2.1 | S | 17.1 | B |
| 2 | 13.1 | B | 17.4 | B |
| 3 | 12.5 | B | 16.8 | B |
| 4 | 13.9 | B | 17.4 | B |
| 5 | 3.5 | S | 15.3 | B |
| 6 | 12.8 | S | 16.2 | B |
| 7 | 3.6 | S | 15.9 | B |
| 8 | 3.1 | S | 17.2 | B |
| 9 | 7.3 | S | 16.4 | B |
| 10 | 13.5 | B | 17.5 | B |
| 11 | 13.4 | B | 17.0 | B |
| 12 | 14.5 | B | 17.6 | B |
| 13 | 12.8 | B | 16.7 | B |
| 14 | 9.4 | S | 17.5 | B |
| 15 | 13.6 | B | 17.5 | B |
| 16 | 13.5 | B | 17.1 | B |
| 17 | 11.8 | S | 14.6 | B |
| 18 | 9.0 | S | 17.6 | B |
| 19 | 13.3 | B | 16.6 | B |
| 20 | 14.1 | B | 18.1 | B |

Example 24: Size 0

| | Standard Suture | | Suture of this Invention | |
|---|---|---|---|---|
| Test | Gage Reading (kg) | Broken Loop (B) or Slippage of Knot (S) | Gage Reading (kg) | Broken Loop (B) or Slippage of Knot (S) |
| 1 | 9.6 | B | 11.0 | B |
| 2 | 9.4 | B | 10.8 | B |
| 3 | 4.2 | S | 10.8 | B |
| 4 | 4.1 | S | 10.5 | B |
| 5 | 3.5 | S | 8.3 | S |
| 6 | 5.4 | S | 11.0 | B |
| 7 | 4.7 | S | 6.8 | S |
| 8 | 6.6 | S | 10.8 | B |
| 9 | 6.4 | S | 6.3 | S |
| 10 | 9.3 | B | 11.0 | B |
| 11 | 9.2 | B | 10.5 | B |
| 12 | 5.7 | S | 10.3 | B |
| 13 | 6.8 | S | 10.8 | B |
| 14 | 6.0 | S | 10.3 | B |
| 15 | 5.7 | S | 10.8 | B |
| 16 | 4.2 | S | 11.3 | B |
| 17 | 4.1 | S | 10.8 | B |
| 18 | 9.8 | B | 10.8 | B |
| 19 | 4.1 | S | 8.0 | B |
| 20 | 4.9 | S | 10.8 | B |

Example 25: Size 2-0

| | Standard Suture | | Suture of this Invention | |
|---|---|---|---|---|
| Test | Gage Reading (kg) | Broken Loop (B) or Slippage of Knot (S) | Gage Reading (kg) | Broken Loop (B) or Slippage of Knot (S) |
| 1 | 2.6 | S | 8.5 | B |
| 2 | 3.5 | S | 9.3 | B |
| 3 | 1.4 | S | 8.7 | B |
| 4 | 4.1 | S | 8.6 | B |
| 5 | 2.4 | S | 8.7 | B |
| 6 | 4.1 | S | 8.6 | B |
| 7 | 1.5 | S | 8.8 | B |
| 8 | 2.2 | S | 8.9 | B |
| 9 | 3.1 | S | 8.4 | B |
| 10 | 6.4 | B | 8.8 | B |
| 11 | 6.0 | B | 9.2 | B |
| 12 | 4.1 | S | 8.8 | B |
| 13 | 2.5 | S | 8.5 | B |
| 14 | 2.4 | S | 9.0 | B |
| 15 | 2.4 | S | 9.3 | B |
| 16 | 4.9 | B | 9.2 | B |
| 17 | 2.1 | S | 8.4 | B |
| 18 | 2.1 | S | 9.1 | B |
| 19 | 4.4 | S | 9.1 | B |
| 20 | 4.8 | S | 9.1 | B |

Example 26: Size 3-0

| | Standard Suture | | Suture of this Invention | |
|---|---|---|---|---|
| | Gage Reading | Broken Loop (B) or Slippage | Gage Reading | Broken Loop (B) or Slippage |

TABLE V-continued

Knot Security of Bioabsorbable Sutures Measured As Loop Pull Strength (kg)

| Test | (kg) | of Knot (S) | (kg) | of Knot (S) |
|---|---|---|---|---|
| 1 | 1.5 | S | 5.3 | B |
| 2 | 3.9 | B | 5.4 | B |
| 3 | 1.2 | S | 5.3 | B |
| 4 | 2.4 | S | 5.3 | B |
| 5 | 3.7 | B | 5.0 | B |
| 6 | 3.9 | S | 5.0 | B |
| 7 | 1.2 | S | 5.0 | B |
| 8 | 4.0 | B | 5.5 | B |
| 9 | 1.4 | S | 5.8 | B |
| 10 | 4.0 | B | 5.3 | B |
| 11 | 2.4 | S | 4.8 | B |
| 12 | 2.7 | S | 6.5 | B |
| 13 | 2.2 | S | 6.3 | B |
| 14 | 2.6 | S | 5.3 | B |
| 15 | 2.9 | S | 5.3 | B |
| 16 | 3.2 | S | 4.8 | B |
| 17 | 3.9 | B | 5.6 | B |
| 18 | 3.7 | B | 4.8 | B |
| 19 | 2.1 | S | 5.0 | B |
| 20 | 2.8 | S | 5.3 | B |

Example 27: Size 4-0

| | Standard Suture | | Suture of this Invention | |
|---|---|---|---|---|
| Test | Gage Reading (kg) | Broken Loop (B) or Slippage of Knot (S) | Gage Reading (kg) | Broken Loop (B) or Slippage of Knot (S) |
| 1 | 2.8 | S | 3.0 | B |
| 2 | 1.5 | S | 3.2 | B |
| 3 | 1.9 | S | 3.0 | B |
| 4 | 2.8 | B | 3.3 | B |
| 5 | 2.7 | B | 3.3 | B |
| 6 | 2.0 | S | 3.3 | B |
| 7 | 0.6 | S | 3.0 | B |
| 8 | 1.0 | S | 3.3 | B |
| 9 | 2.6 | B | 3.3 | B |
| 10 | 3.0 | B | 3.5 | B |
| 11 | 1.4 | S | 3.8 | B |
| 12 | 0.8 | S | 3.3 | B |
| 13 | 3.0 | S | 3.3 | B |
| 14 | 2.6 | B | 2.8 | B |
| 15 | 2.6 | S | 3.3 | B |
| 16 | 1.7 | S | 3.4 | B |
| 17 | 2.6 | B | 3.3 | B |
| 18 | 1.8 | S | 2.8 | B |
| 19 | 3.0 | B | 3.0 | B |
| 20 | 2.8 | B | 2.8 | B |

Example 28: Size 5-0

| | Standard Suture No. 1 | | Standard Suture No. 2 | | Suture of this Invention | |
|---|---|---|---|---|---|---|
| Test | Gage Reading (kg) | Broken Loop (B) or Slippage of Knot (S) | Gage Reading (kg) | Broken Loop (B) or Slippage of Knot (S) | Gage Reading (kg) | Broken Loop (B) or Slippage of Knot (S) |
| 1 | 0.5 | S | 1.0 | S | 2.0 | B |
| 2 | 0.7 | S | 1.7 | B | 2.2 | B |
| 3 | 0.4 | S | 1.6 | B | 2.2 | B |
| 4 | 0.7 | S | 0.5 | S | 2.2 | B |
| 5 | 1.4 | S | 0.3 | S | 2.3 | B |
| 6 | 1.2 | S | 0.4 | S | 2.4 | B |
| 7 | 0.7 | S | 0.6 | S | 2.5 | B |
| 8 | 2.0 | B | 0.2 | S | 2.3 | B |
| 9 | 1.0 | S | 0.5 | S | 2.4 | B |
| 10 | 0.6 | S | 1.5 | B | 2.6 | B |
| 11 | 1.4 | S | 1.3 | S | 2.6 | B |
| 12 | — | — | 1.6 | S | 2.4 | B |
| 13 | — | — | 1.1 | S | 2.2 | B |
| 14 | — | — | — | — | 2.4 | B |
| 15 | — | — | — | — | 2.5 | B |
| 16 | — | — | — | — | 2.2 | B |
| 17 | — | — | — | — | 2.2 | B |
| 18 | — | — | — | — | 2.4 | B |
| 19 | — | — | — | — | 2.5 | B |
| 20 | — | — | — | — | 2.4 | B |

TABLE V-continued

Knot Security of Bioabsorbable Sutures Measured As Loop Pull Strength (kg)

Example 29: Size 6-0

| Test | Standard Suture No. 1 Gage Reading (kg) | Standard Suture No. 1 Broken Loop (B) or Slippage of Knot (S) | Standard Suture No. 2 Gage Reading (kg) | Standard Suture No. 2 Broken Loop (B) or Slippage of Knot (S) | Suture of this Invention Gage Reading (kg) | Suture of this Invention Broken Loop (B) or Slippage of Knot (S) |
|---|---|---|---|---|---|---|
| 1 | 0.7 | B | 0.1 | S | 0.8 | B |
| 2 | 0.7 | S | 0.7 | B | 1.0 | B |
| 3 | 0.3 | S | 0.7 | B | 1.0 | B |
| 4 | 0.8 | B | 0.8 | B | 1.0 | B |
| 5 | 0.2 | S | 0.9 | B | 1.0 | B |
| 6 | 0.8 | B | 0.8 | B | 1.0 | B |
| 7 | — | — | 0.7 | B | 1.0 | B |
| 8 | — | — | 0.3 | S | 1.0 | B |
| 9 | — | — | 0.8 | S | 1.0 | B |
| 10 | — | — | — | — | 1.0 | B |
| 11 | — | — | — | — | 1.0 | B |
| 12 | — | — | — | — | 1.0 | B |
| 13 | — | — | — | — | 1.0 | B |
| 14 | — | — | — | — | 1.1 | B |
| 15 | — | — | — | — | 1.1 | B |
| 16 | — | — | — | — | 1.0 | B |
| 17 | — | — | — | — | 1.0 | B |
| 18 | — | — | — | — | 1.0 | B |
| 19 | — | — | — | — | 1.0 | B |
| 20 | — | — | — | — | 0.8 | B |

Example 30: Size 7-0

| Test | Standard Suture Gage Reading (kg) | Standard Suture Broken Loop (B) or Slippage of Knot (S) | Suture of this Invention Gage Reading (kg) | Suture of this Invention Broken Loop (B) or Slippage of Knot (S) |
|---|---|---|---|---|
| 1 | 0.4 | B | 0.4 | B |
| 2 | 0.3 | B | 0.4 | B |
| 3 | 0.4 | B | 0.3 | B |
| 4 | 0.4 | B | 0.2 | B |
| 5 | 0.4 | S | 0.4 | B |
| 6 | 0.3 | S | 0.4 | B |
| 7 | 0.4 | B | 0.4 | B |
| 8 | 0.3 | S | 0.4 | B |
| 9 | 0.4 | B | 0.4 | B |
| 10 | 0.3 | S | 0.4 | B |
| 11 | 0.3 | B | 0.5 | B |
| 12 | 0.4 | B | 0.4 | B |
| 13 | 0.4 | S | 0.2 | B |
| 14 | 0.3 | S | 0.4 | B |
| 15 | 0.3 | B | 0.5 | B |
| 16 | 0.3 | S | 0.4 | B |
| 17 | 0.4 | B | 0.4 | B |
| 18 | 0.2 | S | 0.4 | B |
| 19 | 0.3 | S | 0.4 | B |
| 20 | 0.2 | S | 0.5 | B |

Example 31: Size 8-0

| Test | Suture of this Invention Gage Reading (kg) | Suture of this Invention Broken Loop (B) or Slippage of Knot (S) |
|---|---|---|
| 1 | 0.3 | B |
| 2 | 0.3 | B |
| 3 | 0.3 | B |
| 4 | 0.3 | B |
| 5 | 0.3 | B |
| 6 | 0.3 | B |
| 7 | 0.3 | B |
| 8 | 0.3 | B |
| 9 | 0.3 | B |
| 10 | 0.3 | B |
| 11 | 0.3 | B |
| 12 | 0.2 | B |
| 13 | 0.3 | B |
| 14 | 0.2 | B |
| 15 | 0.3 | B |
| 16 | 0.3 | B |
| 17 | 0.3 | B |
| 18 | 0.3 | B |
| 19 | 0.3 | B |
| 20 | 0.3 | B |

As the data for Examples 23–30 show, the loop pull strength of the sutures of the invention was consistently higher for all sizes of suture than that of the comparably sized standard sutures. Moreover, only in the relatively few cases did slippage of the know occur prior to loop breakage where the sutures of this invention are concerned whereas slippage was a frequent occurrence in the case of the standard sutures.

For a given size of bioabsorbable suture in accordance with this invention, preferred minimum average loop pull force values at break in kg are as set forth in Table VI below:

VI: Preferred Minimum Average Loop Pull Values for the Bioabsorbable Sutures of this Invention

| Preferred Suture Size | Minimum Average Loop Pull Force (kg) |
|---|---|
| 1 | 13 |
| 2 | 14 |
| 0 | 10 |
| 2–0 | 8 |
| 3–0 | 4 |
| 4–0 | 3 |
| 5–0 | 1.5 |
| 6–0 | 1 |
| 7–0 | 0.4 |
| 8–0 | 0.25 |

EXAMPLE 32

This example is illustrative of a size 2/0 braided glycolide-lactide copolymer suture of this invention filled with a wound healing enhancing amount of an HGF- and carrier/storage stabilizing agent-containing filling composition.

A solution of glycerol (278 gm), calcium lactate (43 gm) and sterile water (370 gm) is prepared. Human Growth Factor HEGF-51 (152.6 mg) (Creative Biomolecules, Inc., Hopkinton, Mass.) was dissolved volumetrically to 25 ml with the above solution to provide a braided suture filling composition. The composition was placed in the syringe pump of a suture coating apparatus. The syringe pump was set to provide the filling composition at a constant rate and the suture speed was adjusted to apply 17ml of filling composition to 200 meters of braid. The target concentration of HGF on the braid is 0.52 mg hEGF/meter or approximately 1.8 mg hEGF/gram of braid. After filling, the braid was immediately passed through a 500 drying column. After filling, the spooled braid was removed to a small chamber and stored under a flowing dry nitrogen atmosphere to remove the water from the solution.

While the foregoing description contains many specifics, these specifics should not be construed as limitations on the scope of the invention, but merely as exemplifications of preferred embodiments thereof. Those skilled in the art will envision many other possible variations that are within the scope and spirit of the invention as defined by the accompanying claims.

What is claimed is:

1. A braided suture possessing a greater pick count and a greater number of sheath yarns and exhibiting reduced tissue drag compared with a suture of substantially equivalent size possessing the following enumerated characteristics:

| Overall Suture Denier | Pick Count | Number of Sheath Yarns | Denier of Individual Filaments | Denier of Core |
|---|---|---|---|---|
| 175 | 40 | 6 | 6 | 25 |
| 259 | 47 | 8 | 2.1 | 29 |
| 300 | 46 | 8 | 6 | 100 |
| 500 | 40 | 8 | 6 | 100 |
| 698 | 52 | 12 | 2.1 | 55 |
| 800 | 50 | 12 | 6 | 200 |
| 1200 | 50 | 16 | 6 | 400 |
| 1500 | 50 | 12 | 6 | 600 |
| 1566 | 50 | 16 | 2.1 | 252 |
| 2000 | 40 | 16 | 6 | 800 |
| 2122 | 44 | 16 | 2.2 | 330. |

2. The braided suture of claim 1 wherein the suture exhibits a level of tissue drag which does not exceed about 60% of the level of tissue drag of the suture of substantially equivalent size possessing the enumerated characteristics.

3. The braided suture of claim 1 wherein the suture exhibits a level of tissue drag which does not exceed about 40% of the level of tissue drag of the suture of substantially equivalent size possessing the enumerated characteristics.

4. The braided suture of claim 1 which exhibits a greater knot security than that of the suture of substantially equivalent size possessing the enumerated characteristics.

5. The braided suture of claim 1 exhibiting a minimum average loop pull force at break in kg as follows:

| Suture Size | Minimum Average Loop Pull Force |
|---|---|
| 1 | 13 |
| 2 | 14 |
| 0 | 10 |
| 2-0 | 8 |
| 3-0 | 4 |
| 4-0 | 3 |
| 5-0 | 1.5 |
| 6-0 | 1 |
| 7-0 | 0.4 |
| 8-0 | 0.25. | said minimum average loop pull force being determined by
 forming knotted loops in sutures,
 pulling each knotted loop until the suture breaks,
 measuring said force at break, and
 averaging the measurements.

6. A braided suture wherein for a given overall suture denier, the range of pick count, number of sheath yarns and denier of individual filaments comprising a sheath yarn for a given size of braided suture are related to each other as follows:

| Overall Suture Denier | Pick Count | Number of Sheath Yarns | Denier of Individual Filaments |
|---|---|---|---|
| from about 50 to about 125 | from about 50 to about 100 | from about 4 to about 16 | from about 0.2 to about 1.8 |
| greater than about 125 to about 200 | from about 50 to about 100 | from about 4 to about 16 | from about 0.2 to about 1.8 |
| greater than about 200 to about 300 | from about 50 to about 100 | from about 4 to about 16 | from about 0.2 to about 6.0 |
| greater than about 300 to about 500 | from about 50 to about 100 | from about 10 to about 20 | from about 0.2 to about 6.0 |
| greater than about 500 to about 800 | from about 50 to about 100 | from about 14 to about 20 | from about 0.2 to about 6.0 |
| greater than about 800 to about 1200 | from about 50 to about 100 | from about 16 to about 32 | from about 0.2 to about 6.0 |
| greater than about 1200 to about 2000 | from about 50 to about 100 | from about 20 to about 36 | from about 0.2 to about 6.0 |
| greater than about 2000 to about 4000 | from about 50 to about 100 | from about 20 to about 36 | from about 0.2 to about 6.0; | wherein the braided suture possesses a greater pick count and/or a greater number of sheath yarns and exhibits reduced tissue drag compared with a suture of substantially equivalent size possessing the following enumerated characteristics:

| Overall Suture Denier | Pick Count | Number of Sheath Yarns | Denier of Individual Filaments | Denier of Core |
|---|---|---|---|---|
| 175 | 40 | 6 | 6 | 25 |
| 259 | 47 | 8 | 2.1 | 29 |
| 300 | 46 | 8 | 6 | 100 |
| 500 | 40 | 8 | 6 | 100 |
| 698 | 52 | 12 | 2.1 | 55 |
| 800 | 50 | 12 | 6 | 200 |
| 1200 | 50 | 16 | 6 | 400 |
| 1500 | 50 | 12 | 6 | 600 |
| 1566 | 50 | 16 | 2.1 | 252 |
| 2000 | 40 | 16 | 6 | 800 |
| 2122 | 44 | 16 | 2.2 | 330. |

7. The braided suture of claim 6 possessing a core.

8. The braided suture of claim 7 wherein the overall suture denier and core denier are related to each other as follows:

| Overall Suture Denier | Denier of Core |
|---|---|
| greater than about 125 to about 200 | from about 20 to about 80 |
| greater than about 200 to about 300 | from about 30 to about 100 |
| greater than about 300 to about 500 | from about 80 to about 150 |
| greater than about 500 to about 800 | from about 150 to about 300 |
| greater than about 800 to about 1200 | from about 250 to about 700 |
| greater than about 1200 to about 2000 | from about 400 to about 1200 |
| greater than about 2000 to about 4000. | from about 800 to about 2400 |

9. The braided suture of claim 8 wherein the overall suture denier and core denier are related to each other as follows:

| Overall Suture Denier | Denier of Core |
|---|---|
| greater than about 125 to | from about 25 to about 50 |

-continued

| Overall Suture Denier | Denier of Core |
|---|---|
| about 200 | |
| greater than about 200 to about 300 | from about 50 to about 80 |
| greater than about 300 to about 500 | from about 80 to about 120 |
| greater than about 500 to about 800 | from about 180 to about 280 |
| greater than about 800 to about 1200 | from about 350 to about 650 |
| greater than about 1200 to about 2000 | from about 500 to about 1000 |
| greater than about 2000 to about 4000. | from about 1000 to about 2200 |

10. A braided suture wherein for a given overall suture denier, the range of pick count, number of sheath yarns and denier of individual filaments comprising a sheath yarn for given size of braided suture are related to each other as follows:

| Overall Suture Denier | Pick Count | Number of Sheath Yarns | Denier of Individual Filaments |
|---|---|---|---|
| greater than about 50 to about 125 | from about 55 to about 80 | from about 6 to about 14 | from about 1.0 to about 1.8 |
| greater than about 125 to about 200 | from about 55 to about 80 | from about 6 to about 14 | from about 1.0 to about 1.8 |
| greater than about 200 to about 300 | from about 55 to about 80 | from about 6 to about 14 | from about 1.0 to about 1.8 |
| greater than about 300 to about 500 | from about 55 to about 80 | from about 12 to about 14 | from about 1.0 to about 1.8 |
| greater than about 500 to about 800 | from about 55 to about 80 | from about 14 to about 18 | from about 1.0 to about 1.8 | wherein the braided suture possesses a greater pick count and/or a greater number of sheath yarns and exhibits reduced tissue drag compared with a suture of substantially equivalent size possessing the following enumerated characteristics:

| Overall Suture Denier | Pick Count | Number of Sheath Yarns | Denier of Individual Filaments | Denier of Core |
|---|---|---|---|---|
| 175 | 40 | 6 | 6 | 25 |
| 259 | 47 | 8 | 2.1 | 29 |
| 300 | 46 | 8 | 6 | 100 |
| 500 | 40 | 8 | 6 | 100 |
| 698 | 52 | 12 | 2.1 | 55 |
| 800 | 50 | 12 | 6 | 200 |
| 1200 | 50 | 16 | 6 | 400 |
| 1500 | 50 | 12 | 6 | 600 |
| 1566 | 50 | 16 | 2.1 | 252 |
| 2000 | 40 | 16 | 6 | 800 |
| 2122 | 44 | 16 | 2.2 | 330. |

11. The braided suture of claim 10 possessing a core.

12. The braided suture of claim 1 possessing a core.

13. The braided suture of claim 1 wherein the braided suture is fabricated from a non-absorbable material.

14. The braided suture of claim 13 wherein the non-absorbable material is cotton, silk, polyamide or polyolefin.

15. The braided suture of claim 1 wherein the individual filaments of the braided suture are fabricated from a bioabsorbable polymer.

16. The braided suture of claim 15 wherein the individual filaments of the braided suture are fabricated from a polymer derived at least in part from one or more monomers selected from the group consisting of glycolic acid, glycolide, lactic acid and lactide.

17. The braided suture of claim 1 wherein the suture is fabricated from a material which is susceptible to hydrolysis, the suture being filled with a filling composition comprising at least one water soluble, liquid polyhydroxy compound and/or ester thereof.

18. The braided suture of claim 17 wherein the water soluble, liquid polyhydroxy compound and/or ester thereof is glycerol.

19. The braided suture of claim 18 wherein the thickener is a saturated aliphatic hydroxycarboxylic acid or salt of the general formula

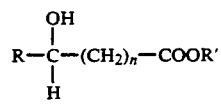

wherein R is hydrogen or a methyl group, R' is hydrogen or a metal selected from the group consisting of alkali metal and alkaline earth metal and n is 0 or 1 and hydrates thereof.

20. The braided suture of claim 17 wherein the water soluble, liquid polyhydroxy compound and/or ester thereof is admixed with a thickener.

21. The braided suture of claim 20 wherein the saturated aliphatic hydroxycarboxylic acid salt is calcium lactate.

22. The braided suture of claim 22 wherein the glycerol is admixed with calcium lactate.

23. The braided suture of claim 1 wherein the braided suture is surface-coated with a composition enhancing one or more functional properties of the suture.

24. The braided suture of claim 1 wherein the suture is surface-coated with a composition which enhances the surface lubricity and/or knot tie-down performance of the suture.

25. The braided suture of claim 24 wherein the composition is a bioabsorbable coating composition obtained by copolymerizing a polyether glycol with a mixture of lactide monomer and glycolide monomer or a preformed copolymer of lactide and glycolide.

26. The braided suture of claim 25 wherein the polyether glycol is selected from the group consisting of low molecular weight polyalkylene glycol and polyethylene oxide-polypropylene oxide copolymer.

27. The braided suture of claim 17 wherein the suture is surface-coated with a composition which enhances the surface lubricity and/or knot tie-down performance of the suture.

28. The braided suture of claim 27 wherein the composition is a bioabsorbable coating composition obtained by copolymerizing a polyether glycol with a mixture of lactide monomer and glycolide monomer or a preformed copolymer lactide and glycolide.

29. The braided suture of claim 28 wherein the polyether glycol is selected from the group consisting of low molecular weight polyalkylene glycol and polyethylene oxide-polypropylene oxide copolymer.

30. The braided suture of claim 1 wherein the suture contains at least one medico-surgically useful substance.

31. The braided suture of claim 30 wherein the medico-surgically useful substance is at least one Human Growth Factor.

32. The braided suture of claim 31 to wherein the Human Growth Factor is combined with a carrier comprising at least one water soluble, liquid polyhydroxy compound and/or ester thereof.

33. The braided suture of claim 32 wherein the polyhydroxy compound is glycerol.

34. The braided suture of claim 32 wherein the carrier further comprises a thickener.

35. The braided suture of claim 34 wherein the thickener is a saturated aliphatic hydroxycarboxylic acid or salt of the general formula

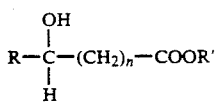

wherein R is hydrogen or a methyl group, R' is hydrogen or a metal selected from the group consisting of alkali metal and alkaline earth metal and n is 0 or 1 and hydrates thereof.

36. The braided suture of claim 35 wherein the thickener is calcium lactate.

37. The braided suture of claim 34 wherein the carrier is glycerol and the thickener is calcium lactate.

38. The braided suture of claim 17 wherein the filling composition includes at least one Human Growth Factor.

39. The braided suture of claim 38 wherein the polyhydroxy compound is glycerol.

40. The braided suture of claim 38 wherein the filling composition includes a thickener.

41. The braided suture of claim 40 wherein the thickener is a saturated aliphatic hydroxycarboxylic acid or salt of the general formula

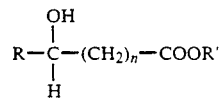

wherein R is hydrogen or a methyl group, R' is hydrogen or a metal selected from the group consisting of alkali metal and alkaline earth metal and n is 0 or 1 and hydrate thereof.

42. The braided suture of claim 41 wherein the thickener is calcium lactate.

43. The braided suture of claim 40 wherein the carrier is glycerol and the thickener is calcium lactate.

44. A braided suture of improved construction wherein for a given overall suture denier, the range of pick count, number of sheath yarns and denier of individual filaments comprising a sheath yarn for a given size of braided suture are related to each other as follows:

| Overall Suture Denier | Pick Count | Number of Sheath Yarns | Denier of Individual Filaments |
|---|---|---|---|
| from about 50 to about 125 | from about 50 to about 100 | from about 4 to about 16 | from about 0.2 to about 1.8 |
| greater than about 125 to about 200 | from about 50 to about 100 | from about 4 to about 16 | from about 0.2 to about 1.8 |
| greater than about 200 to about 300 | from about 50 to about 100 | from about 4 to about 16 | from about 0.2 to about 6.0 |
| greater than about 300 to about 500 | from about 50 to about 100 | from about 10 to about 20 | from about 0.2 to about 6.0 |
| greater than about 500 to about 800 | from about 50 to about 100 | from about 14 to about 20 | from about 0.2 to about 6.0 |
| greater than about 800 to about 1200 | from about 50 to about 100 | from about 16 to about 32 | from about 0.2 to about 6.0 |
| greater than about 1200 to about 2000 | from about 50 to about 100 | from about 20 to about 36 | from about 0.2 to about 6.0 |
| greater than about 2000 to about 4000. | from about 50 to about 100 | from about 20 to about 36 | from about 0.2 to about 6.0 | the suture being fabricated from a material which is susceptible to hydrolysis and filled with a filling composition comprising at least one water soluble, liquid polyhydroxy compound and/or ester thereof.

45. The braided suture of claim 44 possessing a core.

46. The braided suture of claim 45 wherein the overall suture denier and core denier are related to each other as follows:

| Overall Suture Denier | Denier of Core |
|---|---|
| greater than about 125 to about 200 | from about 20 to about 80 |
| greater than about 200 to about 300 | from about 30 to about 100 |
| greater than about 300 to about 500 | from about 80 to about 150 |
| greater than about 500 to about 800 | from about 150 to about 300 |
| greater than about 800 to about 1200 | from about 250 to about 700 |
| greater than about 1200 to about 2000 | from about 400 to about 1200 |
| greater than about 2000 to about 4000. | from about 800 to about 2400 |

47. The braided suture of claim 44 wherein the water soluble, liquid polyhydroxy compound is glycerol.

48. The braided suture of claim 47 wherein the glycerol is admixed with calcium lactate.

49. The braided suture of claim 44 wherein the water soluble, liquid polyhydroxy compound and/or ester thereof is admixed with a thickener.

50. The braided suture of claim 49 wherein the thickener is a saturated aliphatic hydroxycarboxylic acid or salt of the general formula

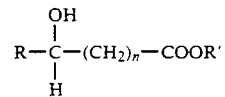

wherein R is hydrogen or a methyl group, R' is hydrogen or a metal selected from the group consisting of alkali metal and alkaline earth metal and n is 0 or 1 and hydrates thereof.

51. The braided suture of claim 50 wherein the saturated aliphatic hydroxycarboxylic acid salt is calcium lactate.

52. The braided suture of claim 44 wherein the braided suture is surface-coated with a composition enhancing one or more functional properties of the suture.

53. The braided suture of claim 44 wherein the suture is surface-coated with a composition which enhances the surface lubricity and/or knot tie-down performance of the suture.

54. The braided suture of claim 53 wherein the composition is a bioabsorbable coating composition obtained by copolymerizing a polyether glycol with a mixture of lactide monomer and glycolide monomer or a preformed copolymer of lactide and glycolide.

55. The braided suture of claim 54 wherein the polyether glycol is selected from the group consisting of low molecular weight polyalkylene glycol and polyethylene oxide-polypropylene oxide copolymer.

56. The braided suture of claim 44 wherein the suture contains at least one medico-surgically useful substance.

57. The braided suture of claim 44 wherein the medico-surgically useful substance is at least one Human Growth Factor.

58. A braided suture possessing a greater pick count and/or a greater number of sheath yarns and exhibiting significantly greater knot security than a suture of substantially equivalent size possessing the following enumerated characteristics:

| Overall Suture Denier | Pick Count | Number of Sheath Yarns | Denier of Individual Filaments | Denier of Core |
|---|---|---|---|---|
| 175 | 40 | 6 | 6 | 25 |
| 259 | 47 | 8 | 2.1 | 29 |
| 300 | 46 | 8 | 6 | 100 |
| 500 | 40 | 8 | 6 | 100 |
| 698 | 52 | 12 | 2.1 | 55 |
| 800 | 50 | 12 | 6 | 200 |
| 1200 | 50 | 16 | 6 | 400 |
| 1500 | 50 | 12 | 6 | 600 |
| 1566 | 50 | 16 | 2.1 | 252 |
| 2000 | 40 | 16 | 6 | 800 |
| 2122 | 44 | 16 | 2.2 | 330. |

59. The braided suture of claim 58 which is bioabsorbable.

60. The braided suture of claim 58 exhibiting a minimum average loop pull force at break in kg as follows:

| Suture Size | Minimum Average Loop Pull Force |
|---|---|
| 1 | 13 |
| 2 | 14 |
| 0 | 10 |
| 2–0 | 8 |
| 3–0 | 4 |
| 4–0 | 3 |
| 5–0 | 1.5 |
| 6–0 | 1 |
| 7–0 | 0.4 |
| 8–0 | 0.25, | said minimum average loop pull force being determined by
 forming knotted loops in sutures,
 pulling each knotted loop until the suture breaks,
 measuring said force at break, and
 averaging the measurement.

61. A braided suture possessing a greater pick count and/or a greater number of sheath yarns and exhibiting reduced chatter compared with a suture of substantially equivalent size possessing the following enumerated characteristics:

| Overall Suture Denier | Pick Count | Number of Sheath Yarns | Denier of Individual Filaments | Denier of Core |
|---|---|---|---|---|
| 175 | 40 | 6 | 6 | 25 |
| 259 | 47 | 8 | 2.1 | 29 |
| 300 | 46 | 8 | 6 | 100 |
| 500 | 40 | 8 | 6 | 100 |
| 698 | 52 | 12 | 2.1 | 55 |
| 800 | 50 | 12 | 6 | 200 |
| 1200 | 50 | 16 | 6 | 400 |
| 1500 | 50 | 12 | 6 | 600 |
| 1566 | 50 | 16 | 2.1 | 252 |
| 2000 | 40 | 16 | 6 | 800 |
| 2122 | 44 | 16 | 2.2 | 330. |

* * * * *